US012617844B2

(12) United States Patent
Araki et al.

(10) Patent No.: US 12,617,844 B2
(45) Date of Patent: May 5, 2026

(54) ANTIBODIES THAT BIND TO CLEAVED FORM OF MUTANT CALRETICULIN, AND DIAGNOSTIC, PREVENTIVE, OR THERAPEUTIC AGENT FOR MYELOPROLIFERATIVE NEOPLASM

(71) Applicants: JUNTENDO EDUCATIONAL FOUNDATION, Bunkyo-ku (JP); MEIJI SEIKA PHARMA CO., LTD., Chuo-ku (JP)

(72) Inventors: Marito Araki, Bunkyo-ku (JP); Yoshihiko Kihara, Bunkyo-ku (JP); Norio Komatsu, Bunkyo-ku (JP)

(73) Assignees: JUNTENDO EDUCATIONAL FOUNDATION, Tokyo (JP); MEIJI SEIKA PHARMA CO., LTD., Tokyo (JP)

( * ) Notice: Subject to any disclaimer, the term of this patent is extended or adjusted under 35 U.S.C. 154(b) by 1127 days.

(21) Appl. No.: 17/434,619

(22) PCT Filed: Feb. 28, 2020

(86) PCT No.: PCT/JP2020/008434
§ 371 (c)(1),
(2) Date: Aug. 27, 2021

(87) PCT Pub. No.: WO2020/175689
PCT Pub. Date: Sep. 3, 2020

(65) Prior Publication Data
US 2022/0098290 A1 Mar. 31, 2022

(30) Foreign Application Priority Data
Feb. 28, 2019 (JP) ................................. 2019-036119

(51) Int. Cl.
*C07K 16/18* (2006.01)
*G01N 33/50* (2006.01)
*G01N 33/574* (2006.01)

(52) U.S. Cl.
CPC .......... *C07K 16/18* (2013.01); *G01N 33/5011* (2013.01); *G01N 33/57426* (2013.01); *C07K 2317/56* (2013.01); *C07K 2317/565* (2013.01)

(58) Field of Classification Search
CPC ................ C07K 16/18; C07K 2317/56; C07K 2317/565; C07K 2317/34; C07K 2317/92; C07K 16/30; G01N 33/5011; G01N 33/57426; G01N 2333/4727; G01N 2500/04; G01N 33/15; G01N 33/50; G01N 33/574; G01N 2500/00; A61K 2039/505; A61P 35/00
See application file for complete search history.

(56) References Cited

U.S. PATENT DOCUMENTS

| | | | |
|---|---|---|---|
| 2015/0079091 A1 | 3/2015 | Kralovics et al. | |
| 2017/0269092 A1 | 9/2017 | Kralovics | |
| 2017/0283473 A1 | 10/2017 | Noelke et al. | |

FOREIGN PATENT DOCUMENTS

| | | |
|---|---|---|
| JP | 2016-537012 A | 12/2016 |
| JP | 2017-62127 A | 3/2017 |
| RU | 2 668 808 C2 | 10/2017 |
| WO | WO 2015-036599 A1 | 3/2015 |
| WO | WO 2016/087314 A2 | 6/2016 |
| WO | WO 2016/087514 A1 | 6/2016 |

OTHER PUBLICATIONS

Griffiths et al. Human anti-self antibodies with high specificity from phage display libraries. EMBO J. Feb. 1993; 12(2):725-34 (Year: 1993).*
Blythe et al. Benchmarking B cell epitope prediction: underperformance of existing methods. Protein Sci. Jan. 2005; 14(1):246-8. (Year: 2005).*
Schreiber et al. 3D-Epitope-Explorer (3DEX): localization of conformational epitopes within three-dimensional structures of proteins. J Comput Chem. Jul. 15, 2005;26(9):879-87. (Year: 2005).*
Gershoni et al. Epitope mapping: the first step in developing epitope-based vaccines. BioDrugs. 2007;21(3):145-56. (Year: 2007).*
Ladner RC. Mapping the epitopes of antibodies. Biotechnol Genet Eng Rev. 2007;24:1-30. (Year: 2007).*
Lin et al. Improved affinity of a chicken single-chain antibody to avian infectious bronchitis virus by site-directed mutagenesis of complementarity-determinig region H3. African J Biotech, 2011, 10(79): 18294-18302. (Year: 2011).*
Stein et al A new monoclonal antibody (CAL2) detects Calreticulin mutations in formalin-fixed and paraffin-embedded bone marrow biopsies. Leukemia. Jan. 2016;30(1):131-5. (Year: 2016).*
Dondelinger et al. Understanding the significance and implications of anitbody numbering and antigen-binding surface/ residue definition. Front Immunol, 2018, 9: 2278. (Year: 2018).*
Pronier et al. Targeting the CALR interactome in myeloproliferative neoplasms. JCI Insight. Nov. 15, 2018;3(22):e122703. (Year: 2018).*
Holmström et al. The calreticulin (CALR) exon 9 mutations are promising targets for cancer immune therapy. Leukemia. Feb. 2018; 32(2):429-437 (Year: 2018).*
Singaporean Search Report and Written Opinion issued Dec. 30, 2022 in Singaporean Patent Application No. 1120210849Y, 10 pages.

(Continued)

*Primary Examiner* — Julie Wu
*Assistant Examiner* — Amber K Faust
(74) *Attorney, Agent, or Firm* — Oblon, McClelland, Maier & Neustadt, L.L.P.

(57) ABSTRACT
A diagnostic, preventive, or therapeutic agent may be used for a myeloproliferative neoplasm. An antibody or a functional fragment thereof that binds to a cleaved mutant CALR protein, may include an antigen-recognition site in (a) a polypeptide chain having an amino acid sequence set forth in SEQ ID NO: 1 or (b) a polypeptide chain having an amino acid sequence having deletion, substitution, or addition of one to several amino acids in SEQ ID NO: 1; and a diagnostic, preventive, or therapeutic agent for a myeloproliferative neoplasm containing the antibody.

12 Claims, 10 Drawing Sheets

Specification includes a Sequence Listing.

(56)            References Cited

OTHER PUBLICATIONS

Kihara et al., "Therapeutic Potential of an Antibody Targeting the Cleaved Form of Mutant Calreticulin in Myeloproliferative Neoplasms.", Blood, Nov. 5, 2020, vol. 136, No. Supplement 1, pp. 9-10 (total 3 pages).

Combined Chinese Office Action and Search Report issued Nov. 28, 2023 in Chinese Patent Application No. 202080017462.8 (with unedited computer-generated English translation). 14 pages.

International Search Report issued on Mar. 31, 2020 in PCT/JP2020/008434 filed on Feb. 28, 2020, 2 pages.

Klampfl et al., "Somatic Mutations of Calreticulin in Myeloproliferative Neoplasms", The New England Journal of Medicine, 2013, vol. 369, No. 25, pp. 2379-2390.

Nangalia et al., "Somatic CALR Mutations in Myeloproliferative Neoplasms with Nonmutated JAK2", The New England Journal of Medicine, 2013, vol. 369, No. 25, pp. 2391-2405.

Araki et al., "Activation of the thrombopoietin receptor by mutant calreticulin in CALR-mutant myeloproliferative neoplasms", Blood, 2016, vol. 127, No. 10, pp. 1307-1316.

Elf et al., "Mutant Calreticulin Requires Both Its Mutant C-terminus and the Thrombopoietin Receptor for Oncogenic Transformation", Cancer Discovery, American Association for Cancer Research, 2016, pp. 368-381 (15 total pages).

Marty et al., "Calreticulin mutants in mice induce an MPL-dependent thrombocytosis with frequent progression to myelofibrosis", Blood, 2016, vol. 127, No. 10, pp. 1317-1324.

Vainchenker et al., "Genetic basis and molecular pathophysiology of classical myeloproliferative neoplasms", Blood, 2017, vol. 129, No. 6, pp. 667-679.

Vannucchi et al., "Calreticulin mutation-specific immunostaining in myeloproliferative neoplasms: pathogenetic insight and diagnostic value", Leukemia, 2014, vol. 28, pp. 1811-1816.

Combined Russian Office Action and Search Report issued Jun. 14, 2023 in Russian Application No. 2021128127, (with English Translation), 26 pages.

Melikyan et al., "Classical Ph-negative myeloproliferative neoplasia. Materials of the 56th Congress of the American Hematological Society", Clinical Oncohematology, 2015, vol. 8, No. 2, 32 pages (with English explanations about Figures are included in several pages).

Rudikoff et al., "Single amino acid substitution altering antigen-binding specificity", Proc. Natl. Acad. Sci. USA, vol. 79 No. 6, 1979-1983, 5 pages.

Brown et al. "Tolerance of single, but not multiple, amino acid replacements in antibody VH CDR 2: a means of minimizing B cell wastage from somatic hypermutation?", J. Immunol., 1996, vol. 156 No. 9 (submitting English Abstract only), 1 page.

Lloyd et al., "Modelling the human immune response: performance of a 1011 human antibody repertoire against a broad panel of therapeutically relevant antigens", Protein Engineering, Design & Selection, 2009, vol. 22, 10 pages.

Edwards, et al., "The Remarkable Flexibility of the Human Antibody Repertoire; Isolation of Over One Thousand Different Antibodies to a Single Protein, BLyS", Journal of Molecular Biology, 2003, vol. 334, No. 1, 16 pages.

Wegmann, "Targeting cytokines in asthma therapy: could IL-37 be a solution?", Expert Review of Respiratory Medicine, 2017, vol. 11, No. 9, 4 pages.

Subortseva et al. "Myelodysplastic/myeloproliferative diseases", Oncohematology, 2016, vol. 11, 10 pages (with English abstract).

George et al. "Differential Effects of Anti-b2-Glycoprotein I Antibodies on Endothelial Cells and on the Manifestations of Experimental Antiphospholipid Syndrome", Circulation, 1998, vol. 97, 7 pages.

Y. N. Abdiche et al. "Antibodies Targeting Closely Adjacent or Minimally Overlapping Epitopes Can Displace One Another", PLoS One, 2017, vol. 12 No. 1, 22 pages.

* cited by examiner

Figure 14

HEAVY-CHAIN VARIABLE REGION AMINO ACID SEQUENCE

CLONE B3

QVQLQQSGAELVKPGSSVKISCKASGYTFTRNFIHWIKQQPGNGLEWIGWIFPGDGDTEYNQKFNGKATLTADK
SSSTAYMQLSSLTSEDSAVYFCARGNYNYEYFDYWGQGVMVTVSS

CLONE C6

QVQLQQSGAELVKPGSSVKISCKASGYTFTSYFVHWIKQQPGDGLEWIGWIYPGDGDTEYNHKFNGKSTLTADR
SSSTAYMQLSSLTSEDSAVYFCARGNYYDGREVMDAWGQGASVTVSS

CLONE G1

QVQLQQSGAELVKPGSSVKISCKASGYTFTSYFVHWIKQQPGDGLEWIGWIYPGDGDTEYNQKFNGKATLTADR
SSSTAYMQLSSLTSEDSAVYFCARGNYYDGREVMDAWGQGASVTVSS

Figure 15

LIGHT-CHAIN VARIABLE REGION AMINO ACID SEQUENCE

CLONE B3

DIQMTQSPASLSASLGETVSIECLASEDIYSYLAWYQQKPGKSPQLLIFAANRLQDGVPSRFSGSGSGTQFSLK
ISGMQPEDEGDYFCLQGSKFPYTFGPGTKLELN

CLONE C6

DVVLTQTPPTLSATIGQSVSISCRSSQSLLDSDGETYLNWLLQRPGQSPQLLIYSVSNLESGVPNRFSGSGSET
DFTLKISGMEAEDLGVYYCMQATHGPYTFGAGTKLELK

CLONE G1

DVVLTQTPPTLSATIGQSVSISCRSSQSLLDSDGETYLNWLLQRPGQCPQLLIYSVSNLESGVPNRFSGSGSET
DFTLKISGVEAEDLGVYYCMQGTHGPYTFGAGTKLELK

Figure 16

HEAVY-CHAIN VARIABLE REGION NUCLEOTIDE SEQUENCE

CLONE B3
CAGGTACAGCTGCAGCAATCTGGGGCTGAACTGGTGAAGCCTGGGTCCTCAGTGAAAATTTCCTGCAAGGCTTC
TGGCTACACCTTCACCCGTAACTTTATACACTGGATAAAACAGCAGCCTGGAAATGGCCTTGAGTGGATTGGGT
GGATTTTTCCTGGAGATGGTGATACAGAGTACAATCAAAAGTTCAATGGGAAGGCAACACTCACTGCAGACAAA
TCGTCCAGCACAGCCTATATGCAGCTCAGCAGCCTGACATCTGAGGACTCTGCAGTCTATTTCTGTGCAAGAGG
AAATTACAACTACGAGTACTTTGATTACTGGGGCCAAGGAGTCATGGTCACAGTCTCCTCA

CLONE C6
CAGGTACAGCTGCAGCAATCTGGGGCTGAACTGGTGAAGCCTGGGTCCTCAGTGAAAATTTCCTGCAAGGCTTC
TGGCTACACCTTCACCAGTTACTTTGTGCACTGGATAAAACAGCAGCCTGGAGATGGCCTTGAGTGGATTGGGT
GGATTTATCCTGGAGATGGTGATACAGAGTACAATCACAAGTTCAATGGGAAGTCAACACTCACTGCAGACAGA
TCCTCCAGTACAGCCTATATGCAGCTCAGCAGCCTGACATCTGAGGACTCTGCAGTCTATTTCTGTGCAAGAGG
GAATTACTATGATGGTCGGGAAGTTATGGATGCCTGGGGTCAAGGAGCTTCAGTCACTGTCTCCTCA

CLONE G1
CAGGTACAGCTGCAGCAATCTGGGGCTGAACTGGTGAAGCCTGGGTCCTCAGTGAAAATTTCCTGCAAGGCTTC
TGGCTACACCTTCACCAGTTACTTTGTGCACTGGATAAAACAGCAGCCTGGAGATGGCCTTGAGTGGATTGGGT
GGATTTATCCTGGAGATGGTGATACAGAGTACAATCAAAAGTTCAATGGGAAGGCAACACTCACTGCAGACAGA
TCCTCCAGTACAGCCTATATGCAGCTCAGCAGCCTGACATCTGAGGACTCTGCAGTCTATTTCTGTGCAAGAGG
GAATTACTATGATGGTCGGGAAGTTATGGATGCCTGGGGTCAAGGAGCTTCAGTCACTGTCTCCTCA

Figure 17

LIGHT-CHAIN VARIABLE REGION NUCLEOTIDE SEQUENCE

CLONE B3

GACATCCAGATGACACAGTCTCCGGCTTCCCTGTCTGCATCTCTGGGAGAAACTGTCTCCATCGAGTGTCTAGC
AAGTGAGGACATTTACAGTTATTTAGCATGGTATCAACAGAAGCCAGGGAAATCTCCTCAGCTCCTGATCTTTG
CTGCAAATAGGTTGCAAGATGGGGTCCCATCACGGTTCAGTGGCAGTGGATCTGGCACACAGTTTTCTCTCAAG
ATCAGCGGCATGCAACCTGAAGATGAAGGGGATTATTTCTGTCTACAGGGTTCCAAGTTTCCGTACACCTTTGG
ACCTGGGACCAAGCTGGAACTGAAC

CLONE C6

GATGTTGTGCTGACCCAGACTCCACCCACTTTATCGGCTACCATTGGACAATCGGTCTCCATCTCTTGCAGGTC
AAGTCAGAGTCTCTTAGATAGTGATGGAGAAACCTATTTAAATTGGTTGCTACAGAGGCCAGGCCAATCTCCAC
AGCTTCTAATTTATTCGGTCTCCAACCTGGAATCTGGGGTCCCCAACAGGTTCAGTGGCAGTGGGTCAGAAACA
GATTTCACACTCAAAATCAGTGGAATGGAGGCTGAAGATTTGGGAGTTTACTACTGCATGCAAGCTACCCATGG
TCCGTACACGTTTGGAGCTGGGACCAAGCTGGAACTGAAA

CLONE G1

GATGTTGTGCTGACCCAGACTCCACCCACTTTATCGGCTACCATTGGACAATCGGTCTCCATCTCTTGCAGGTC
AAGTCAGAGTCTCTTAGATAGTGATGGAGAAACCTATTTAAATTGGTTGCTACAGAGGCCAGGCCAATGTCCAC
AGCTTCTAATTTATTCGGTATCCAACCTGGAATCTGGGGTCCCCAACAGGTTCAGTGGCAGTGGGTCAGAAACA
GATTTCACACTCAAAATCAGTGGAGTGGAGGCTGAAGATTTGGGAGTTTACTACTGCATGCAAGGTACCCATGG
TCCGTACACGTTTGGAGCTGGGACCAAGCTGGAACTGAAA

ANTIBODIES THAT BIND TO CLEAVED FORM OF MUTANT CALRETICULIN, AND DIAGNOSTIC, PREVENTIVE, OR THERAPEUTIC AGENT FOR MYELOPROLIFERATIVE NEOPLASM

CROSS-REFERENCE TO RELATED APPLICATIONS

The present application is the national stage of international application PCT/JP2020/008434, filed on Feb. 28, 2020, and claims the benefit of the filing date of Japanese Appl. No. 2019-036119, filed on Feb. 28, 2019, the content of each of which is incorporated by reference.

REFERENCE TO A SEQUENCE LISTING

This application contains a Sequence Listing in computer readable form (CRF) submitted as an ASCII text file named "538416US_051525_ST25.txt", created on May 15, 2025 and having a size of 24,549 bytes. The contents of the ASCII text file are incorporated herein by reference in their entirety.

TECHNICAL FIELD

The present invention relates to a diagnostic, preventive, or therapeutic agent for a myeloproliferative neoplasm.

BACKGROUND ART

In a part of patients with Philadelphia-negative myeloproliferative neoplasms (MPNs), nucleotide deletion or insertion is found in exon 9 of the calreticulin (CALR) gene (Non Patent Literatures 1 and 2). It has been already revealed that the mutant CALR protein produced by a CALR mutant gene has oncogenicity independently causing a myeloproliferative neoplasm (MPN) by constantly activating a thrombopoietin receptor (Non Patent Literatures 3 to 6).

The CALR gene mutation found in MPN patients is a frameshift mutation that is necessarily localized in the last exon, and a shift in the amino acid reading frame by the frameshift mutation is always +1. From these things, a sequence that is not present in the wild type is present at the carboxyl-terminal of the mutant CALR protein, and in particular, 44 amino acids of the carboxyl-terminal are common to almost all of the mutant CALR proteins. As an example thereof, FIG. 1 shows comparison of the sequences of carboxyl-terminals of 52-nucleotide deletion type (Del 52), which is the most frequent mutation among CALR gene mutations found in MPN patients, and 5-nucleotide insertion type (Ins 5), which is the next most frequent mutation, with the corresponding region of the wild-type CALR protein.

Since the mutant CALR protein causing occurrence of an MPN is expressed in tumor cells, it has been suggested that there is a possibility that the sequence specific to the mutant CALR protein caused by the frameshift mutation becomes a marker for diagnosis or a therapeutic target as a neo-antigen (Patent Literatures 1 and 2).

CITATION LIST

Patent Literature

Patent Literature 1: JP-A-2016-537012
Patent Literature 2: WO2016/087514A

Non Patent Literature

Non Patent Literature 1: Klampfl T, Gisslinger H, Harutyunyan A S, et al., Somatic mutations of calreticulin in myeloproliferative neoplasms, The New England journal of medicine, 2013, 369:2379-90
Non Patent Literature 2: Nangalia J, Massie C E, Baxter E J, et al., Somatic CALR mutations in myeloproliferative neoplasms with nonmutated JAK2, The New England journal of medicine, 2013, 369:2391-405
Non Patent Literature 3: Araki M, Yang Y, Masubuchi N, et al., Activation of the thrombopoietin receptor by mutant calreticulin in CALR-mutant myeloproliferative neoplasms, Blood, 2016, 127:1307-16
Non Patent Literature 4: Elf S, Abdelfattah N S, Chen E, et al., Mutant Calreticulin Requires Both Its Mutant C-terminus and the Thrombopoietin Receptor for Oncogenic Transformation, Cancer Discov., 2016, 6:368-81
Non Patent Literature 5: Marty C, Pecquet C, Nivarthi H, et al., Calreticulin mutants in mice induce an MPL-dependent thrombocytosis with frequent progression to myelofibrosis, Blood, 2016, 127:1317-24
Non Patent Literature 6: Vainchenker W, Kralovics R., Genetic basis and molecular pathophysiology of classical myeloproliferative neoplasms, Blood, 2017, 129: 667-79

SUMMARY OF INVENTION

Technical Problem

However, it was proved that an antibody that recognizes a sequence (neo-antigen) specific to the mutant CALR protein appearing by the frameshift mutation cannot correctly detect the mutant CALR protein in cell extract or on a cell surface.

Accordingly, it is an object of the present invention to provide detection methods capable of correctly detecting a mutant CALR gene and a protein of an MPN, a diagnostic, preventive, or therapeutic agent for an MPN, and a method for screening for an MPN therapeutic agent.

Solution to Problem

The present inventors further performed functional analysis of the mutant CALR proteins and, as a result, found that many of the expressed mutant CALR proteins are cleaved in a sequence (FIG. 1) specific to mutant proteins and that mutant CALR proteins in which most of the sequence inferred as the neo-antigen has been lost are largely expressed. Accordingly, an antibody that specifically recognizes a significantly short amino acid sequence located at the amino-terminal side of the cleavage site in the neo-antigen was produced, and it was verified that cleaved mutant CALR proteins were expressed not only in cultured cells but also in patient peripheral blood cells and patient platelets. Furthermore, it was revealed that by using this antibody, the detection sensitivity for the mutant CALR protein on a cell surface is dramatically improved and, in addition, excellent MPN therapeutic effect is obtained. From these findings, it was revealed that in diagnosis or therapy of MPN patients having a CALR gene mutation, pharmaceutical products showing higher performance can be developed by detecting or targeting not only the full-length type (non-cleavage type) but also mutant CALR proteins including cleavage types. In addition, it was strongly suggested that the effect of a pharmaceutical product targeting the sequence that is lost by cleavage can be increased by preventing cleavage of the mutant CALR protein, and the present invention has been accomplished.

That is, the present invention provides the following [1] to [14].

[1] An antibody or a functional fragment thereof that binds to a cleaved mutant CALR protein, comprising an antigen-recognition site in (a) a polypeptide chain consisting of an amino acid sequence set forth in SEQ ID NO: 1 or in (b) a polypeptide chain consisting of an amino acid sequence having deletion, substitution, or addition of one to several amino acids in SEQ ID NO: 1.

[2] The antibody or the functional fragment thereof that binds to the cleaved mutant CALR protein according to aspect [1], wherein the antibody or the functional fragment thereof is selected from the following (c), (d), and (e):

(c) an antibody in which CDR1, CDR2, and CDR3 of the immunoglobulin VH chain are polypeptides consisting of the amino acid sequences set forth in SEQ ID NOs: 17, 18, and 19, respectively, or amino acid sequences having deletion, substitution, or addition of one to several amino acids in the amino acid sequences set forth in SEQ ID NOS: 17, 18, and 19; and CDR1, CDR2, and CDR3 of the immunoglobulin VL chain are polypeptides consisting of the amino acid sequences set forth in SEQ ID NOs: 26, 27, and 28, respectively, or amino acid sequences having deletion, substitution, or addition of one to several amino acids in the amino acid sequences set forth in SEQ ID NOs: 26, 27, and 28;

(d) an antibody in which CDR1, CDR2, and CDR3 of the immunoglobulin VH chain are polypeptides consisting of the amino acid sequences set forth in SEQ ID NOs: 20, 21, and 22, respectively, or amino acid sequences having deletion, substitution, or addition of one to several amino acids in the amino acid sequences set forth in SEQ ID NOs: 20, 21, and 22; and CDR1, CDR2, and CDR3 of the immunoglobulin VL chain are polypeptides consisting of the amino acid sequences set forth in SEQ ID NOs: 29, 30, and 31, respectively, or amino acid sequences having deletion, substitution, or addition of one to several amino acids in the amino acid sequences set forth in SEQ ID NOs: 29, 30, and 31; and (e) an antibody in which CDR1, CDR2, and CDR3 of the immunoglobulin VH chain are polypeptides consisting of the amino acid sequences set forth in SEQ ID NOs: 23, 24, and 25, respectively, or amino acid sequences having deletion, substitution, or addition of one to several amino acids in the amino acid sequences set forth in SEQ ID NOs: 23, 24, and 25; and CDR1, CDR2, and CDR3 of the immunoglobulin VL chain are polypeptides consisting of the amino acid sequences set forth in SEQ ID NOs: 32, 33, and 34, respectively, or amino acid sequences having deletion, substitution, or addition of one to several amino acids in the amino acid sequences set forth in SEQ ID NOS: 32, 33, and 34.

[3] The antibody or the functional fragment thereof that binds to the cleaved mutant CALR protein according to aspect [1] or [2], selected from the following (C), (D), and (E):

(C) an antibody comprising an immunoglobulin VH chain consisting of an amino acid sequence set forth in SEQ ID NO: 5 or an amino acid sequence having deletion, substitution, or addition of one to several amino acids in the amino acid sequence set forth in SEQ ID NO: 5 and an immunoglobulin VL chain consisting of an amino acid sequence set forth in SEQ ID NO: 8 or an amino acid sequence having deletion, substitution, or addition of one to several amino acids in the amino acid sequence set forth in SEQ ID NO: 8;

(D) an antibody comprising an immunoglobulin VH chain consisting of an amino acid sequence set forth in SEQ ID NO: 6 or an amino acid sequence having deletion, substitution, or addition of one to several amino acids in the amino acid sequence set forth in SEQ ID NO: 6 and an immunoglobulin VL chain consisting of an amino acid sequence set forth in SEQ ID NO: 9 or an amino acid sequence having deletion, substitution, or addition of one to several amino acids in the amino acid sequence set forth in SEQ ID NO: 9; and (E) an antibody comprising an immunoglobulin VH chain consisting of an amino acid sequence set forth in SEQ ID NO: 7 or an amino acid sequence having deletion, substitution, or addition of one to several amino acids in the amino acid sequence set forth in SEQ ID NO: 7 and an immunoglobulin VL chain consisting of an amino acid sequence set forth in SEQ ID NO: 10 or an amino acid sequence having deletion, substitution, or addition of one to several amino acids in the amino acid sequence set forth in SEQ ID NO: 10.

[4] An antibody or a functional fragment thereof that competes with the antibody according to aspect [2] or [3] for binding to an amino acid sequence portion set forth in SEQ ID NO: 1 in a cleavage mutant CALR protein.

[5] A pharmaceutical composition comprising the antibody or the functional fragment thereof according to any one of aspects [1] to [4].

[6] The pharmaceutical composition according to aspect [5], wherein the pharmaceutical composition is a diagnostic, preventive, or therapeutic agent for a myeloproliferative neoplasm.

[7] A method for detecting a myeloproliferative neoplasm-related mutant CALR protein, comprising detecting the following polypeptide (a) or (b) in a biological sample:

(a) a polypeptide consisting of an amino acid sequence set forth in SEQ ID NO: 1; or (b) a polypeptide consisting of an amino acid sequence having deletion, substitution, or addition of one to several amino acids in SEQ ID NO: 1.

[8] The method for detecting a mutant CALR protein according to aspect [7], wherein the detection of the polypeptide (a) or (b) is immunological detection using the antibody or the functional fragment thereof according to any one of aspects [1] to [4].

[9] A method for screening for a myeloproliferative neoplasm therapeutic agent, comprising screening for a drug that binds to the following polypeptide (a) or (b):

(a) a polypeptide consisting of an amino acid sequence set forth in SEQ ID NO: 1; or (b) a polypeptide consisting of an amino acid sequence having deletion, substitution, or addition of one to several amino acids in SEQ ID NO: 1.

[10] A diagnostic method for a myeloproliferative neo-
plasm, comprising detecting the following polypeptide
(a) or (b) in a biological sample:
(a) a polypeptide consisting of an amino acid sequence
set forth in SEQ ID NO: 1; or
(b) a polypeptide consisting of an amino acid sequence
having deletion, substitution, or addition of one to
several amino acids in SEQ ID NO: 1.
[11] The diagnostic method according to aspect [10],
wherein the detection of the polypeptide (a) or (b) is
immunological detection using the antibody or the
functional fragment thereof according to any one of
aspects [1] to [4].
[12] A preventive or therapeutic method for a myelopro-
liferative neoplasm, comprising administering the anti-
body or a functional fragment thereof according to any
one of aspects [1] to [4].
[13] The antibody or the functional fragment thereof
according to any one of aspects [1] to [4], for use in
diagnosis of a myeloproliferative neoplasm.
[14] Use of the antibody or the functional fragment
thereof according to any one of aspects [1] to [4], for
producing a diagnostic agent for a myeloproliferative
neoplasm.

Effects of Invention

By using an antibody having an antigen-recognition site
(epitope) in the above-mentioned polypeptide chain (a) or
(b), it is possible to detect a mutant CALR protein caused by
cleavage of a mutant CALR protein and to dramatically
improve the detection sensitivity for a mutant CALR protein
on a cell surface. Accordingly, the detection sensitivity of an
MPN is dramatically improved by using the MPN diagnostic
agent of the present invention. In addition, an MPN can be
specifically prevented or treated by using this antibody. In
addition, an MPN therapeutic agent can be screened by
screening for a drug that binds to the polypeptide (a) or (b).

BRIEF DESCRIPTION OF DRAWINGS

FIG. 2 is at the amino-terminal side of the CALR
protein and the carboxyl-terminal side of mutant CALR
proteins. The antibody that recognizes the sequence at the
amino-terminal side of the CALR protein is a commercially
available antibody (anti-CALR antibody) that recognizes an
amino acid sequence at the amino-terminal side of the
mutation site of the mutant CALR proteins. In addition, the
antibody that recognizes the sequence of the carboxyl-
terminal of each mutant CALR protein is a commercially
available antibody (anti-mutant CALR antibody) that rec-
ognizes an amino acid sequence that has been newly gen-

Figure 3:
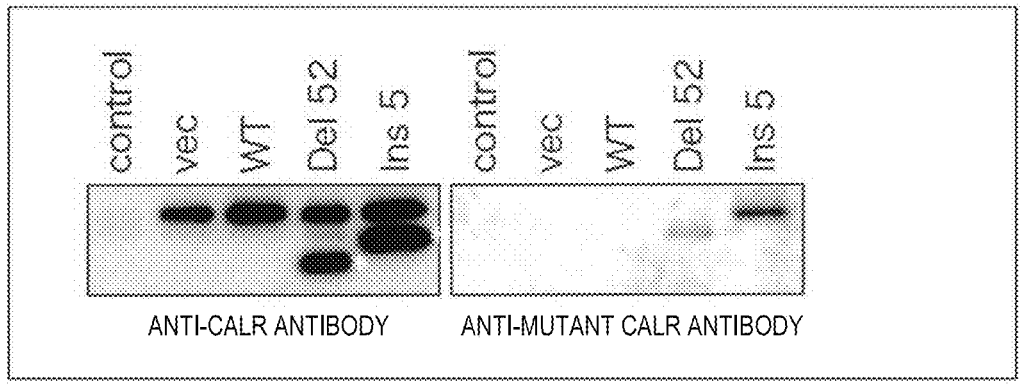
Figure 4:
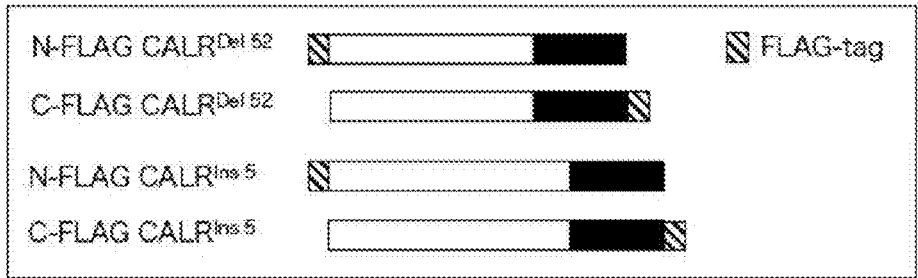
Figure 5:
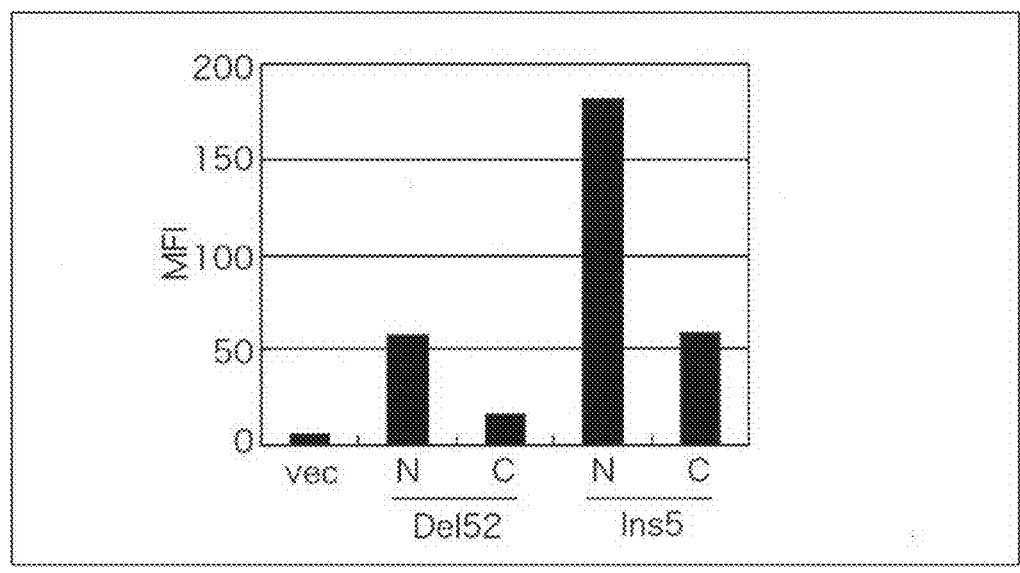
Figure 6:
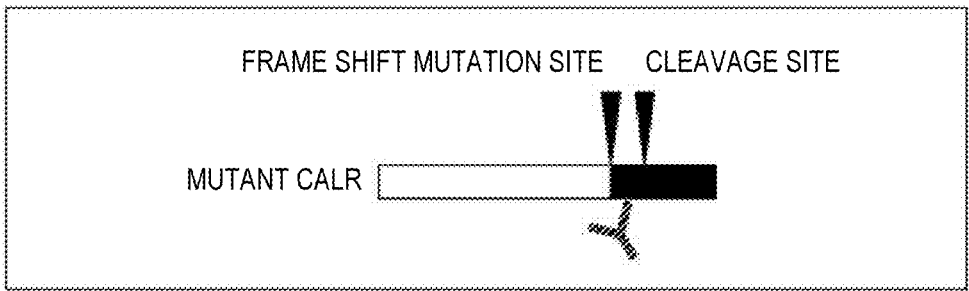
Figure 7:
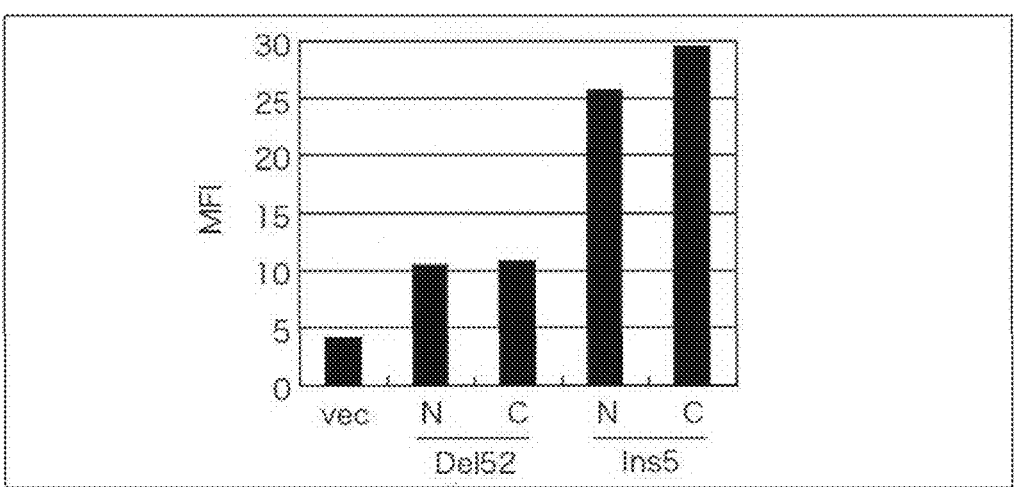
Figure 8:
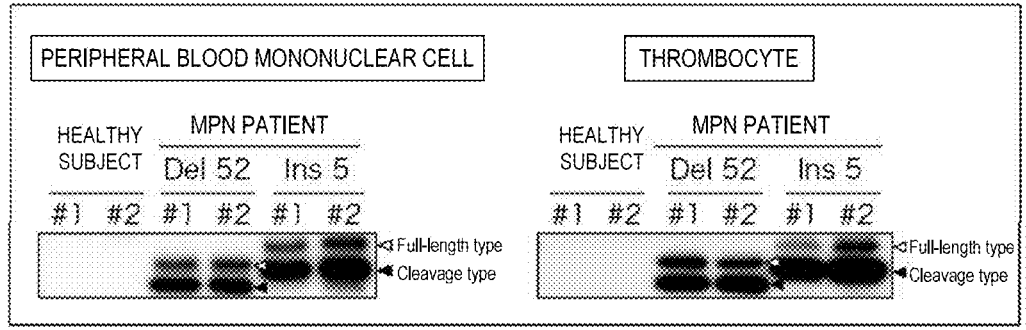
Figure 9:
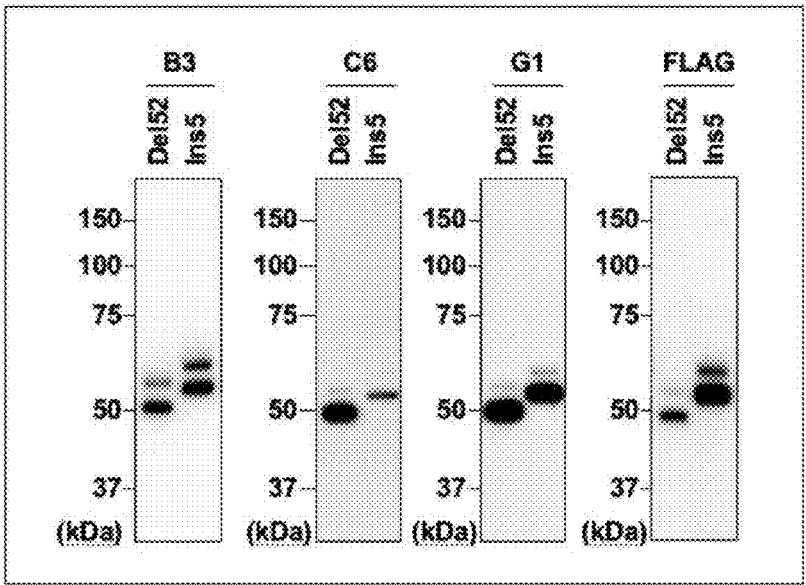
Figure 10:
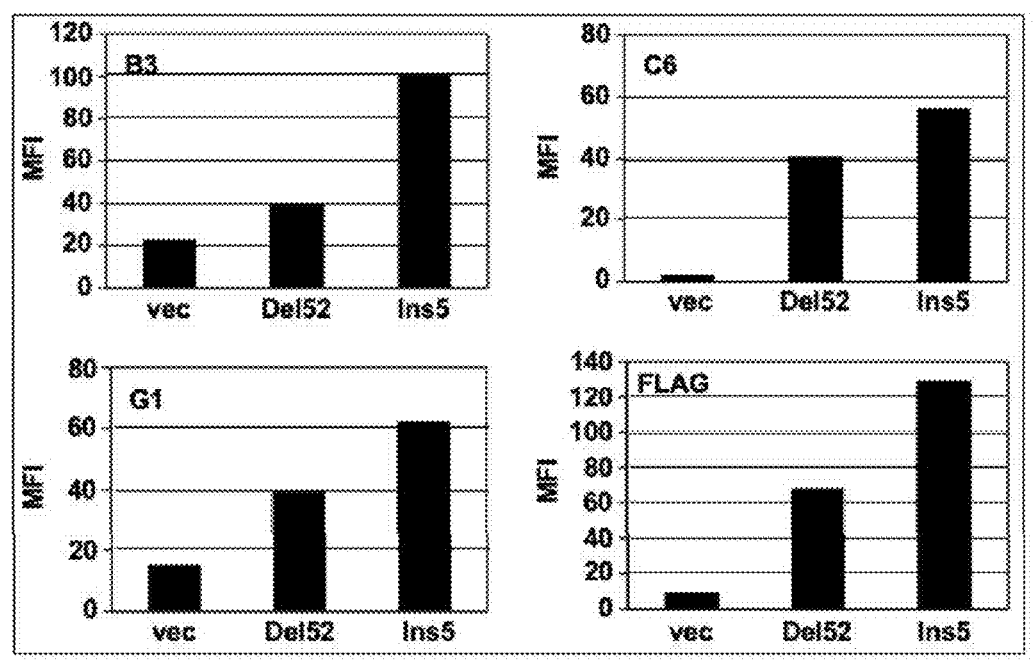

6 erated on the carboxyl-terminal side of the CALR protein by
mutation of the nucleotide sequence.
FIG. 3 is a diagram showing the results of immunoblot
analysis of proteins secreted from UT-7/TPO cells (Komatsu
N. et al., Blood, 1996, 87, 4552-4556) using the antibodies
of FIG. 2. Since vec is a cell transfected with an expression
vector only, an endogenous CALR protein is detected as in
UT-7/TPO cell/CALR (WT). In the Del 52 type and the Ins
5 type, a mutant CALR protein having a molecular weight
smaller than that of the full-length mutant CALR protein
detected by the anti-mutant CALR antibody is detected by
the anti-CALR antibody only (asterisk in the drawing).
Incidentally, since the full-length mutant CALR protein of
the Ins 5 type is electrophoresed to substantially the same
position as the endogenous wild-type CALR protein, the Ins
5 type cannot be specifically detected by the anti-CALR
antibody.
FIG. 4 is a schematic diagram showing proteins in which
FLAG-tags are fused to the amino (N) terminals and the
carboxyl (C) terminals of typical mutant CALR proteins, the
Del 52 type and the Ins 5 type. The mutant-type-specific
sequences are illustrated by black color, and the FLAG-tags
are illustrated by oblique lines.
FIG. 5 is a graph showing the results of measurement of
the amounts of mutant CALR proteins on cell surfaces by
flow cytometry analysis using an anti-FLAG antibody. In the
cells expressing the mutant CALR protein having the
FLAG-tag at the N-terminal on which a tag remains, regard-
less of the presence or absence of cleavage, a strong signal
was detected, compared to the cells in which the C-terminal
FLAG is cut off by cleavage occurring in the sequence
specific to the mutant CALR protein. Incidentally, a differ-
ence caused by that the expression level of the Del 52 type
is lower than that of the Ins 5 type is observed.
FIG. 6 shows an antibody that recognizes a mutant-type-
specific sequence at the amino-terminal side of the cleavage
site of the protein produced in a mutant CALR protein-
specific sequence (black).
FIG. 7 shows the results of flow cytometry analysis of the
cells used in FIG. 3 using the antibody of FIG. 6. The
difference in recognition, which is caused by the positions at
which the FLAG-tag is fused, disappeared. Incidentally, a
difference that the expression level of the Del 52 type is
lower than that of the Ins 5 type is observed.
FIG. 8 is a diagram showing detection of a cleavage type
CALR protein in myeloproliferative neoplasm patient cells.
Cell extracts prepared from patient cells were analyzed by
immunoblotting using an antibody that recognizes an amino
acid sequence at the amino-terminal side of the cleavage site
of a protein produced in a mutant CALR protein-specific
sequence. In peripheral blood mononuclear cells and plate-
lets of myeloproliferative neoplasm patients having CALR
gene mutation, expression of the cleavage mutant CALR
protein that can be recognized by the antibody was detected.
FIG. 9 is a diagram showing that all of clone B3, C6, and
G1 antibodies recognize the full-length and cleavage mutant
CALR proteins. The diagram shows the results of immuno-
blot analysis of proteins secreted from UT-7/TPO cells using
the clone B3 antibody and clone C6 and G1 antibodies. Both
the full-length types of the Del 52 type and the Ins 5 type
each fused with a FLAG-tag at downstream of the signal
sequence at the amino-terminal and the cleavage types
having lower molecular weights are also detected by any of
the B3, C6, and G1 antibodies, as in the anti-FLAG anti-
body.
FIG. 10 is a diagram showing that all of the clone B3, C6,
and G1 antibodies recognize the mutant CALR proteins on cell surfaces. The diagram shows the results of measurement of the amounts of mutant CALR proteins on cell surfaces of UT-7/TPO cells expressing a Del 52 type or Ins 5 type mutant CALR protein fused with a FLAG tag and UT-7/TPO/vec cells transfected with an expression vector only by flow cytometry analysis using a clone B3 antibody and clone C6 and G1 antibodies. Incidentally, since the expression level of the Del 52 type is lower than that of the Ins 5 type, a difference in the signal intensity due to the type of mutation is observed.

Figure 11:
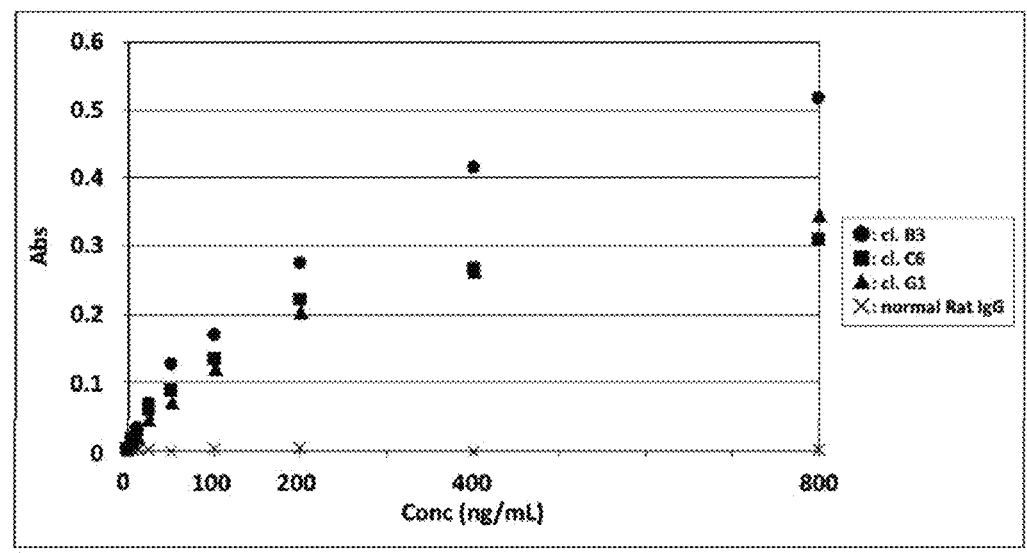

FIG. 11 is a graph showing the results of evaluation of the binding performance of clone B3, C6, and G1 antibodies to a mutant CALR protein. Specificity of binding of the clone B3 antibody, the clone C6 and G1 antibodies, and rat IgG as a control to the Del 52 type mutant CALR protein was evaluated by an ELISA method. Concentration dependent specific binding to the mutant CALR protein was detected in all of the clone B3, C6, and G1 antibodies.

Figure 12:
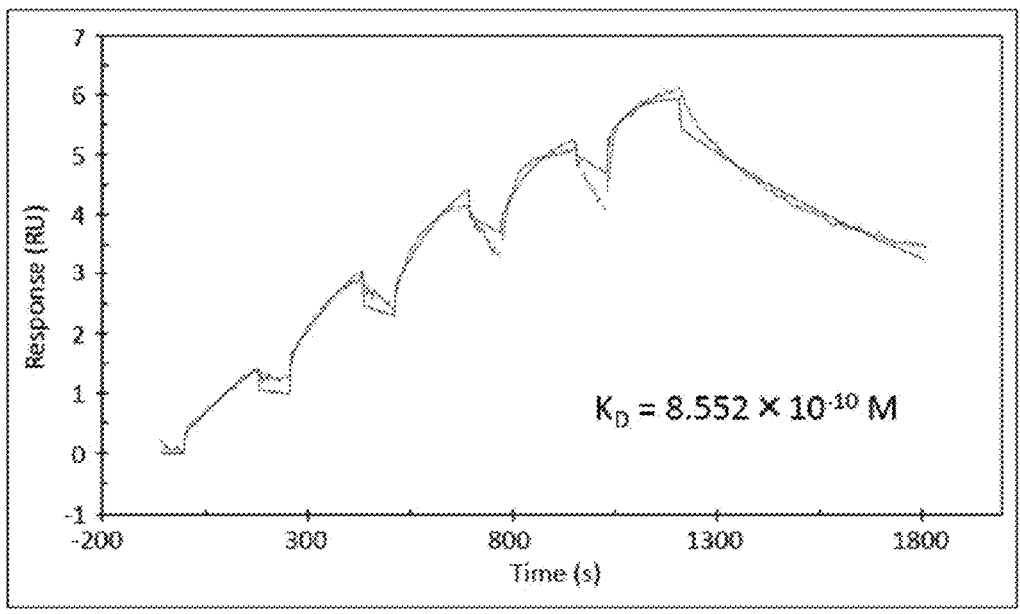

FIG. 12 is a graph showing the results of evaluation of binding strength of the clone B3 antibody to the antigen used for production of the antibody by surface plasmon resonance analysis. The binding strength of the clone B3 antibody and the antigen used for production of the antibody was evaluated by surface plasmon resonance analysis.

Figure 13A:
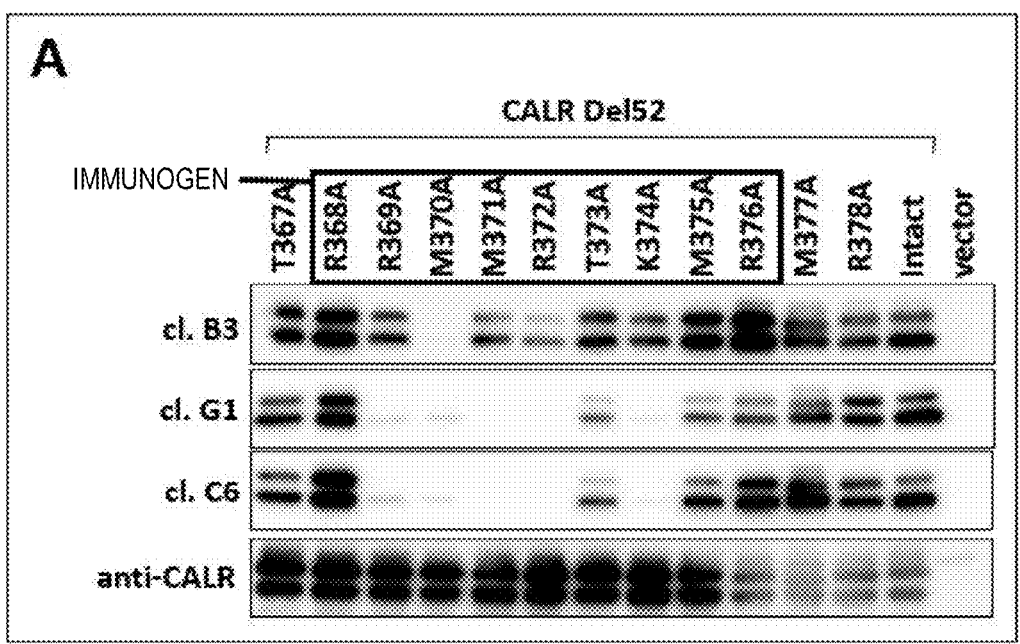

FIG. 13A is a diagram showing the results of identification of the antigen-recognizing sequences of the clone B3, C6, and G1 antibodies by immunoblotting. Proteins each having alanine (A) substituted for an amino acid in the Del 52 type mutant CALR protein shown in the diagram were expressed, and the reactivities of the respective antibodies to the proteins were evaluated by immunoblotting. Intact indicates the Del 52 type mutant CALR protein not having the amino acid substitution. The amino acids surrounded by a thick black line are antigen sequences used for production of the antibodies.

Figure 13B:
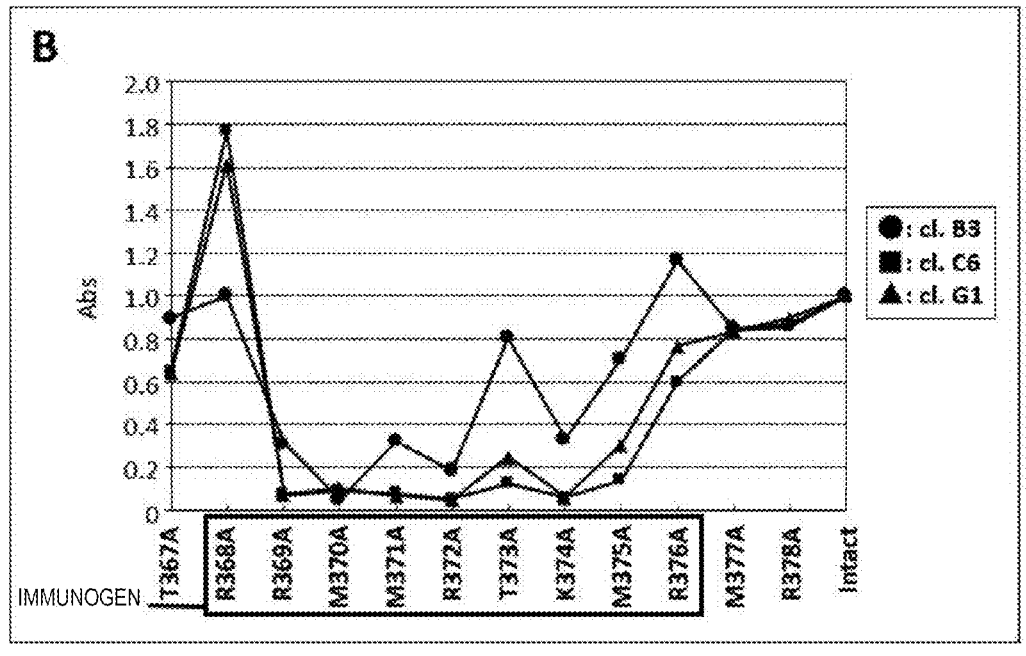

FIG. 13B is a diagram showing the results of identification of the antigen-recognizing sequences of the clone B3, C6, and G1 antibodies by an ELISA method. The reactivities of the respective antibodies to the same proteins as ones in FIG. 13A were evaluated by an ELISA method. Intact indicates the Del 52 type mutant CALR protein not having the amino acid substitution. The amino acids surrounded by a thick black line are antigen sequences used for production of the antibodies.

FIG. 14 is a diagram showing the amino acid sequences of the heavy-chain variable regions of the antibodies (B3, C6, and G1) of the present invention which are respectively identified by SEQ ID NOS: 5, 6 and 7.

FIG. 15 is a diagram showing the amino acid sequences of the light-chain variable regions of the antibodies (B3, C6, and G1) of the present invention which are respectively identified by SEQ ID NOS: 8, 9 and 10.

FIG. 16 is a diagram showing the nucleotide sequences of the heavy-chain variable regions of the antibodies (B3, C6, and G1) of the present invention which are respectively identified by SEQ ID NOS: 11, 12 and 13.

FIG. 17 is a diagram showing the nucleotide sequences of the light-chain variable regions of the antibodies (B3, C6, and G1) of the present invention which are respectively identified by SEQ ID NOS: 14, 15 and 16.

Figure 18:
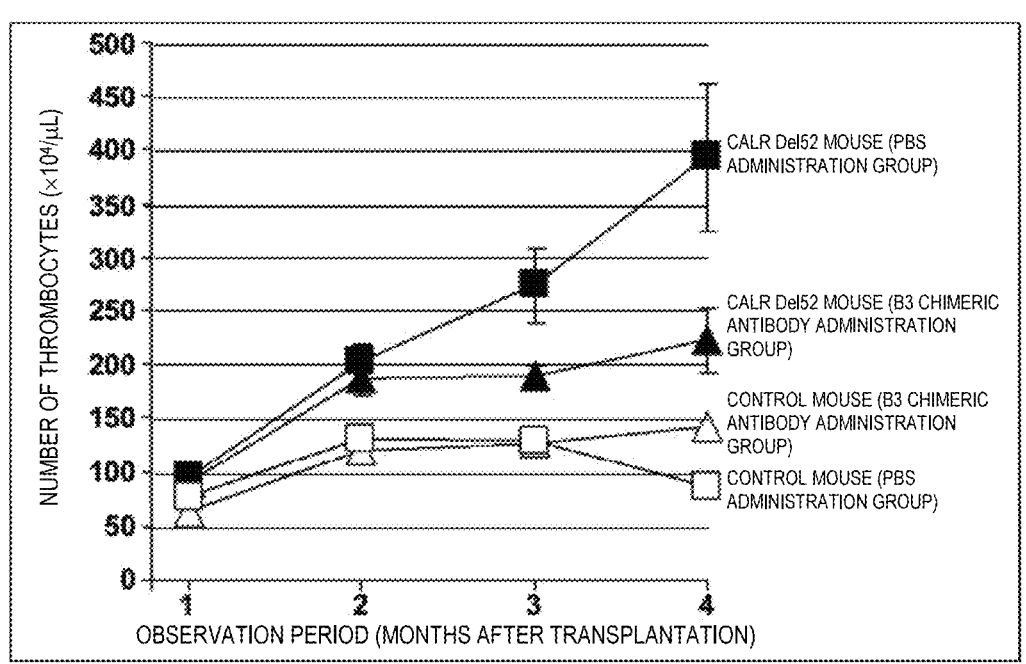

FIG. 18 is a diagram showing the therapeutic effect on MPN model mice by a B3 mouse chimeric antibody. A B3 chimeric antibody or a solvent (PBS) was administered to myeloproliferative neoplasm model mice (CALR Del 52 mouse) produced by transplantation of hematopoietic stem cells expressing the Del 52 type mutant CALR protein or control mice produced by transplantation of hematopoietic stem cells transfected with a control vector every week from the 9th week after the transplantation, and the effect of suppressing the thrombocytosis characteristic to the myeloproliferative neoplasm model mice was evaluated.

DESCRIPTION OF EMBODIMENTS

The polypeptide (a) or (b) of the present invention that is used in a method for detection of an MPN-related mutant CALR protein and used in a diagnostic method and as a target of prevention or therapy of an MPN is a polypeptide remaining on the carboxyl-terminal side after a sequence (44 amino acids common to the mutant CALR proteins in FIG. 1) specific to the mutant CALR proteins is cleaved.

Figure 1:
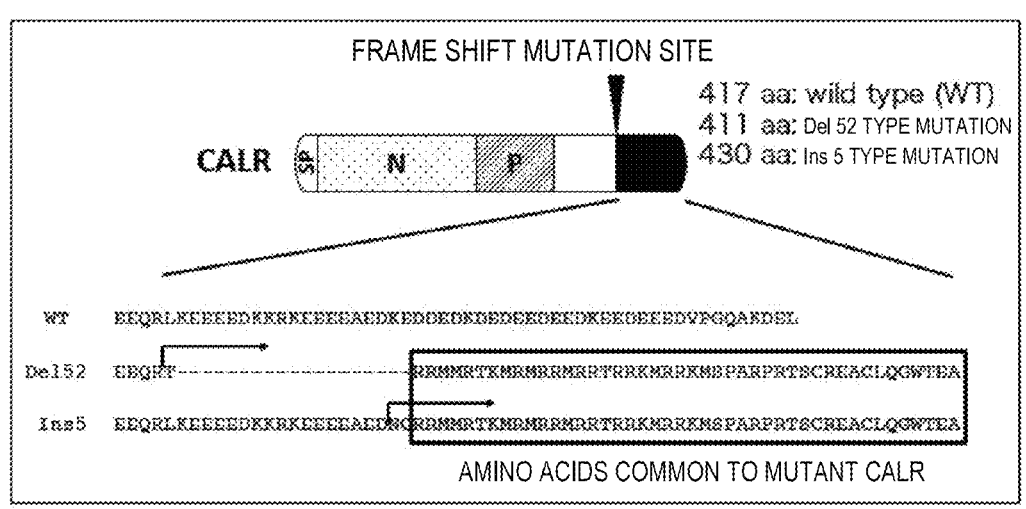
FIG. 1 is a diagram showing characteristics of mutant
CALR proteins. The CALR gene mutation responsible for
the development of patients with myeloproliferative neo-
plasms is +1 frameshift mutation, and an amino acid
sequence common to mutant proteins is found in the car-
boxyl-terminal of the mutant CALR proteins produced as
the results of the mutation. SP: signal sequence, N: N
domain, and P: P domain. The arrow indicates the site at
which amino acid sequences different from the wild-type
(WT) sequence start. Wild type (WT) sequence comprises
SEQ ID NO: 2, residues 363-417. DEL 152 comprises SEQ
ID NO: 3, residues 363-411. Ina 5 comprises residues
363-400 of SEQ ID NO: 4.

The wild-type CALR protein includes the amino acid sequence (SEQ ID NO: 2) shown in FIG. 1. In addition, a 52-nucleotide deletion type (Del 52), which is the most frequent mutation among the CALR gene mutations, includes the amino acid sequence (SEQ ID NO: 3) shown in FIG. 1. In addition, a 5-nucleotide insertion type (Ins 5), which is the next most frequent mutation among the CALR gene mutations, includes the amino acid sequence (SEQ ID NO: 4) shown in FIG. 1. In addition, the region surrounded by the frame in FIG. 1 is an amino acid sequence common to the most of mutant CALR proteins. The cleavage mutant CALR protein includes only 13 amino acids at the amino-terminal side of this common region. The present inventors have found that this common region is cleaved to generate cleavage mutant CALR proteins and that most of the common region is lost from the mutant CALR proteins.

The polypeptide (a) consists of the amino acid sequence set forth in SEQ ID NO: 1. The amino acid sequence having deletion, substitution, or addition of one to several amino acids as the polypeptide (b) is preferably an amino acid sequence having deletion, substitution, or addition of one to four amino acids, more preferably an amino acid sequence having deletion, substitution, or addition of one to three amino acids, in SEQ ID NO: 1. More specifically, an amino acid sequence having deletion of three amino acids from the carboxy-terminal side of SEQ ID NO: 1 is more preferable. In addition, the identity between the amino acid sequence of the polypeptide (b) and the amino acid sequence of SEQ ID NO: 1 is preferably 80% or more, more preferably 85% or more, and further preferably 90% or more.

In a method for detecting an MPN-related mutant CALR protein and a diagnostic, preventive, or therapeutic method for an MPN of the present invention, an antibody or a functional fragment thereof that binds to the polypeptide (a) or (b) in a biological sample is used.

The antibody may be any antibody having an antigen-recognition site (epitope) in the polypeptide chain (a) or (b) and may bind to only a cleavage mutant CALR protein or may bind to both a cleavage mutant CALR protein and a full-length mutant CALR protein, and the antibody is preferably an antibody specific to "mutant CALR protein" that binds to both the cleavage mutant CALR protein and the full-length mutant CALR protein. Specific examples of the antibody include antibodies selected from the following (c), (d), and (e):

(c) an antibody in which CDR1, CDR2, and CDR3 of the immunoglobulin VH chain are polypeptides consisting of the amino acid sequences set forth in SEQ ID NOs: 17, 18, and 19, respectively, or amino acid sequences having deletion, substitution, or addition of one to several amino acids in the amino acid sequences set forth in SEQ ID NOs: 17, 18, and 19; and CDR1, CDR2, and CDR3 of the immunoglobulin VL chain are polypeptides consisting of the amino acid sequences set forth in SEQ ID NOs: 26, 27, and 28, respectively, or amino acid sequences having deletion, substitution, or addition of one to several amino acids in the amino acid sequences set forth in SEQ ID NOS: 26, 27, and 28;

(d) an antibody in which CDR1, CDR2, and CDR3 of the immunoglobulin VH chain are polypeptides consisting of the amino acid sequences set forth in SEQ ID NOs: 20, 21, and 22, respectively, or amino acid sequences having deletion, substitution, or addition of one to several amino acids in the amino acid sequences set forth in SEQ ID NOs: 20, 21, and 22; and CDR1, CDR2, and CDR3 of the immunoglobulin VL chain are polypeptides consisting of the amino acid sequences set forth in SEQ ID NOs: 29, 30, and 31, respectively, or amino acid sequences having deletion, substitution, or addition of one to several amino acids in the amino acid sequences set forth in SEQ ID NOs: 29, 30, and 31; and (e) an antibody in which CDR1, CDR2, and CDR3 of the immunoglobulin VH chain are polypeptides consisting of the amino acid sequences set forth in SEQ ID NOs: 23, 24, and 25, respectively, or amino acid sequences having deletion, substitution, or addition of one to several amino acids in the amino acid sequences set forth in SEQ ID NOs: 23, 24, and 25; and CDR1, CDR2, and CDR3 of the immunoglobulin VL chain are polypeptides consisting of the amino acid sequences set forth in SEQ ID NOs: 32, 33, and 34, respectively, or amino acid sequences having deletion, substitution, or addition of one to several amino acids in the amino acid sequences set forth in SEQ ID NOs: 32, 33, and 34.

The amino acid sequence having deletion, substitution, or addition of one to several amino acids in each of the amino acid sequences respectively set forth in SEQ ID NOs: 17 to 34 is preferably an amino acid sequence having deletion, substitution, or addition of one to four amino acids, more preferably an amino acid sequence having deletion, substitution, or addition of one to three amino acids, and further preferably an amino acid sequence having deletion, substitution, or addition of one or two amino acids, in SEQ ID NOs: 17 to 34. In addition, the identity between each of the amino acid sequences respectively set forth in SEQ ID NOs: 17 to 34 and an amino acid sequence having deletion, substitution, or addition of one to several amino acids of the corresponding amino acid sequence is preferably 80% or more, more preferably 85% or more, and further preferably 90% or more.

The antibody having an antigen-recognition site (epitope) in the polypeptide chain (a) or (b) is further preferably an antibody selected from the following (C), (D), and (E):

(C) an antibody comprising an immunoglobulin VH chain consisting of the amino acid sequence set forth in SEQ ID NO: 5 or an amino acid sequence having deletion, substitution, or addition of one to several amino acids in the amino acid sequence set forth in SEQ ID NO: 5 and an immunoglobulin VL chain consisting of the amino acid sequence set forth in SEQ ID NO: 8 or an amino acid sequence having deletion, substitution, or addition of one to several amino acids in the amino acid sequence set forth in SEQ ID NO: 8;

(D) an antibody comprising an immunoglobulin VH chain consisting of the amino acid sequence set forth in SEQ ID NO: 6 or an amino acid sequence having deletion, substitution, or addition of one to several amino acids in the amino acid sequence set forth in SEQ ID NO: 6 and an immunoglobulin VL chain consisting of the amino acid sequence set forth in SEQ ID NO: 9 or an amino acid sequence having deletion, substitution, or addition of one to several amino acids in the amino acid sequence set forth in SEQ ID NO: 9; and (E) an antibody comprising an immunoglobulin VH chain consisting of the amino acid sequence set forth in SEQ ID NO: 7 or an amino acid sequence having deletion, substitution, or addition of one to several amino acids in the amino acid sequence set forth in SEQ ID NO: 7 and an immunoglobulin VL chain consisting of the amino acid sequence set forth in SEQ ID NO: 10 or an amino acid sequence having deletion, substitution, or addition of one to several amino acids in the amino acid sequence set forth in SEQ ID NO: 10.

The amino acid sequence having deletion, substitution, or addition of one to several amino acids in each of the amino acid sequences respectively set forth in SEQ ID NOs: 5 to 10 is preferably an amino acid sequence having deletion, substitution, or addition of one to ten amino acids, more preferably an amino acid sequence having deletion, substitution, or addition of one to eight amino acids, and further preferably an amino acid sequence having deletion, substitution, or addition of one to five amino acids, in SEQ ID NOs: 5 to 10. In addition, the identity between each of the amino acid sequences set forth in SEQ ID NOs: 5 to 10 and an amino acid sequences having deletion, substitution, or addition of one to several amino acids of the corresponding amino acid sequence set forth in SEQ ID NOs: 5 to 10 is preferably 80% or more, more preferably 85% or more, and further preferably 90% or more.

The antibody of the present invention includes the sequences of each CDR of the antibodies (c) to (e) or the sequences of immunoglobulin VH region and VL region of the antibodies (C) to (E), and amino sequences of the regions other than these regions are not particularly limited. Accordingly, the antibody of the present invention may be an antibody of a mammal other than a rat, such as a human antibody or may be a humanized antibody. More specifically, the antibody may be a chimeric antibody composed of the variable regions of the heavy-chain and light-chain of an antibody of a mammal other than human, for example, a rat and the constant regions of the heavy-chain and light-chain of a human antibody, and such an antibody can be prepared by ligating a DNA encoding the variable region of a rat antibody with a DNA encoding the constant region of a human antibody, incorporating this into an expression vector, and introducing the vector into a host for production. A humanized antibody is also referred to as a reshaped human antibody and is obtained by transplanting the CDR of a non-human mammal antibody, for example, a rat antibody to the CDR of a human antibody, and a general gene recombination technique therefor is also known. In a specific example, a DNA sequence designed so as to ligate the CDR of a rat antibody with the framework region (FR) of a human antibody is synthesized from several oligonucleotides produced so as to include a portion overlapping the terminal portion by the PCR method. The resulting DNA is ligated with a DNA encoding a human antibody constant region, then it is incorporated into an expression vector, and the expression vector is introduced into a host for producing a humanized antibody (see European Patent Application Publication No. EP239400 and International Patent Application Publication No. WO96/02576). The human antibody FR that is ligated via the CDR is selected so that the CDR forms a favorable antigen-binding site. As needed, an amino acid of the FR of the variable region of an antibody may be substituted so that the CDR of the reshaped human antibody forms an appropriate antigen-binding site (Sato, K. et al., Cancer Res., 1993, 53, 851-856).

In addition, methods for preparing human antibodies are also known. For example, human lymphocytes are sensitized with a desired antigen or a cell expressing a desired antigen in vitro, and the sensitized lymphocytes are fused with human myeloma cells, such as U266, to obtain a desired human antibody having a binding activity to the antigen (see JP-B-1-59878). In addition, a desired human antibody can be obtained by immunizing a transgenic animal having all repertories of human antibody genes with a desired antigen (see WO 93/12227, WO 92/03918, WO 94/02602, WO 94/25585, WO 96/34096, and WO 96/33735). Furthermore, a technique of obtaining a human antibody by panning using a human antibody library is also known. For example, a variable region of a human antibody is expressed as a single chain antibody (scFv) on the surface of a phage by a phage display method, and the phage that binds to the antigen can be selected. By analyzing the gene of the selected phage, the DNA sequence encoding the variable region of the human antibody that binds to the antigen can be determined. If the DNA sequence of the scFv that binds to the antigen is revealed, a human antibody can be obtained by producing an appropriate expression vector containing the sequence. These methods are already well known, and WO 92/01047, WO 92/20791, WO 93/06213, WO 93/11236, WO 93/19172, WO 95/01438, and WO 95/15388 can be referred to.

The class of the antibody is not particularly limited, and antibodies having any of isotypes, such as IgG, IgM, IgA, IgD, and IgE, are included. Considering, for example, the ease of purification, IgG is preferable.

Examples of functional fragments include low molecular weight antibodies, such as antibody fragments, and modified antibodies. Specific examples of the antibody fragment include Fab, Fab', F(ab')₂, Fv, ScFv, and diabodies.

In addition, among the antibodies of the present invention, the antibody that is used for detecting the polypeptide (a) or (b) may be any antibody that binds to these polypeptides. Alternatively, the antibody that is used for prevention or therapy of an MPN is preferably an antibody that binds to the polypeptide (a) or (b) and has a cytotoxic activity.

The antibody that binds to the cleavage mutant CALR protein may be any antibody that binds to a polypeptide chain including the sequence set forth in SEQ ID NO: 1 and is preferably an antibody that competes with at least one of the above-mentioned antibodies and functional fragments thereof for binding to the amino acid sequence portion set forth in SEQ ID NO: 1 in the cleavage mutant CALR protein.

Here, the biological sample used in the detection is, for example, a sample that is a biological sample collected from a subject and includes the polypeptide (a) or (b). Specifically, examples of the sample include whole blood, plasma, serum, lymphocytes, lymph fluid, platelets, mononuclear cells, granulocytes, body fluids such as saliva and urine, and tissue samples (bone marrow fluid and bone marrow tissue) obtained by bone marrow biopsy.

Examples of the method for detecting the polypeptide (a) or (b) include liquid chromatography mass spectrometry, an immunological method, and a method using a low or medium molecule having specific binding ability or a nucleic acid or a nucleic acid derivative, and an immunological method is preferred because of its ease and high sensitivity.

The immunological method is preferably an immunological method using an antibody or a functional fragment thereof including an antigen-recognition site (epitope) in the polypeptide chain (a) or (b). The epitope in the polypeptide chain (a) or (b) may be any sequence present in the polypeptide chain (a) or (b) and is preferably a peptide including three or more consecutive amino acids in the polypeptide chain (a) or (b) and more preferably a peptide including five or more consecutive amino acids in the polypeptide chain (a) or (b).

The antibody to be used in the immunological method may be any antibody that is obtained using a peptide including, for example, three or more consecutive amino acids in the polypeptide chain (a) or (b) as the antigen and may be a polyclonal antibody or a monoclonal antibody, and a monoclonal antibody is preferable. Here, the monoclonal antibody can be manufactured by, for example, preparing antibody-producing cells by sensitization with a peptide including three or more consecutive amino acids in the polypeptide chain (a) or (b), fusing the antibody-producing cells with myeloma cells to produce hybridomas, selecting a clone producing the target antibody, and multiplying this cell.

As the immunological method, for example, any of immunochromatography, enzyme-labeled immunoassay (EIA), radioimmunoassay (RIA), coagulation method, nephelometry, flow cytometry, tissue immunostaining, and immunoblotting such as western blotting can be used. Here, the immunoblotting is a method in which a polypeptide is transferred on a membrane and the polypeptide on the membrane is detected by an antibody. In detection of the antibody, for example, an enzyme label or a fluorescent label is used.

If the polypeptide (a) or (b) is detected in a biological sample, it can be judged that the biological sample is a biological sample derived from a myeloproliferative neoplasm patient.

The MPN diagnostic agent of the present invention contains an antibody having an antigen recognition site (epitope) in the polypeptide chain (a) or (b). This antibody is preferably the above-described antibody.

In addition, the MPN diagnostic agent of the present invention may include, for example, a buffer and a measurement protocol, in addition to the antibody.

The pharmaceutical composition, such as an MPN preventive or therapeutic agent, of the present invention at least contains the above-described antibody and can be manufactured by formulation together with a pharmaceutically acceptable carrier through, for example, mixing, dissolving, emulsifying, encapsulating, or lyophilization.

The MPN as the target of prevention or therapy by the pharmaceutical composition of the present invention is preferably an MPN in which mutant CALR is detected.

Suitable formulations for oral administration are, for example, a liquid prepared by dissolving an effective amount of the antibody of the present invention in a diluent such as water or physiological saline, a capsule, granule, powder, or tablet containing an effective amount of the antibody as a solid or granules, a suspension prepared by suspending an effective amount of the antibody in an appropriate dispersion medium, and an emulsion prepared by dispersing and emulsifying a solution of an effective amount of the antibody in an appropriate dispersion medium.

For parenteral administration, the antibody of the present invention can be formulated into a dosage form, such as an injectable solution, suspension, emulsion, cream, ointment, inhalant, and suppository, together with pharmaceutically acceptable solvent, excipient, binder, stabilizer, dispersant, etc. In an injectable prescription, the antibody of the present invention can be dissolved in an aqueous solution, prefer-ably a physiologically compatible buffer, such as Hanks' solution, Ringer's solution, or a physiological saline buffer. Furthermore, the pharmaceutical product of the present invention can form, for example, a suspension, a solution, or an emulsion in an oily or aqueous vehicle. Alternatively, the antibody of the present invention is manufactured in a powder form, and an aqueous solution or suspension may be prepared using sterile water or the like before use. In inhalation administration, the antibody of the present inven-tion is powdered and is mixed with an appropriate base, such as lactose or starch, to form a powder mixture. A suppository prescription can be manufactured by mixing the antibody of the present invention with a common suppository base, such as cacao butter. Furthermore, the therapeutic agent of the present invention can be prescribed as a sustained release formulation by encapsulation with a polymer matrix or the like.

The method for screening for an MPN therapeutic agent of the present invention is characterized by screening for an antibody, protein, a low or medium molecule, a nucleic acid, or a nucleic acid derivative that recognizes the polypeptide (a) or (b). Specifically, development of an antibody drug having an antibody-dependent cytotoxic activity or a complement-dependent cytotoxic activity using an antibody that recognizes the polypeptide (a) or (b) is exemplified. The above-described antibody of the present invention is an example of the antibody drug obtained by the screening method of the present invention. In addition to this, it is exemplified to develop an antitumor agent that delivers, for example, a low or medium molecular weight compound, a nucleic acid or nucleic acid derivative, or a protein having a cytotoxicity effect specifically to tumor cells through production of a low or medium molecular weight com-pound, a nucleic acid or nucleic acid derivative, or a protein that specifically binds to the polypeptide (a) or (b).

EXAMPLES

Next, the present invention will be described in more detail with reference to examples but is not limited to these examples.

Test Example 1

(1) Material and Test Method

[1] Anti-CALR Antibody

Rabbit monoclonal antibody clone D3E6 (Cat #12238) manufactured by Cell Signaling Technology, Inc.

[2] Anti-Mutant CALR Antibody

Mouse monoclonal antibody clone CAL2 (Cat #DIA-CAL) manufactured by Dianova GmbH

[3] Antibody that Recognizes Mutant CALR Protein at the Amino-Terminal Side of Cleavage Site A peptide having cysteine at the carboxyl-terminal or the amino-terminal of the amino acid sequence (RRMMRTKMR) included in SEQ ID NO: 1 was synthe-sized and was conjugated to a carrier protein, keyhole limpet hemocyanin (KLH). The conjugate was immunized to 8-week old female WKY/Izm rats, and after booster immunization, the lymphocytes were collected. The lymphocytes were cell-fused with mouse myeloma SP2 cells by a PEG method, and hybridomas were obtained by culturing in a selective medium. The specificity of antibodies in the culture supernatant was screened by an ELISA method using the immunized peptide or purified protein to obtain hybridomas (clones B3, C6, and G1) producing antibodies that bind to mutant CALR proteins including a cleavage type. Antibod-ies (B3 antibody, C6 antibody, and G1 antibody) produced by these hybridomas were purified and used in tests.

[4] Test Method

Human megakaryoblastic leukemia cell line UT-7/TPO was transfected with a vector expressing a Del 52 or Ins 5 type mutant CALR protein, a vector expressing wild-type CALR as a control, or an empty vector. The resulting UT-7/TPO/CALR Del 52 and UT-7/TPO/CALR Ins 5 cells neoplastically proliferating, UT-7/TPO/CALR (WT) cells, and UT-7/TPO/vec cells were respectively seeded at a density of $6.0\times10^5$ cells/mL in Opti-MEM medium (Thermo Fisher Scientific K.K., Cat #31985070) and were cultured in 5% $CO_2$ at 37° C. for 32 hours. On this occasion, UT-7/TPO/CALR WT and UT-7/TPO/vec cells were cultured in a medium containing 10 ng/mL thrombopoietin (TPO). The culture supernatants were obtained by removing the cells from the culture solutions by centrifugation (15,000 g×10 min, 4° C.), the resulting fractions were each heat-treated in the presence of a reducing agent, then developed on a gel by SDS polyacrylamide electrophoresis, electrically transferred on a polyvinylidene fluoride (PVDF) membrane, and reacted with a TBS-T solution (0.1% Tween-20, 150 mM sodium chloride, 50 mM Tris-HCl, pH 7.5) containing 5% skimmed milk at room temperature for 1 hour, followed by reaction at 4° C. overnight with a 5% BSA/TBS-T solution containing an antibody that recognizes both the wild-type and the mutant-type (rabbit monoclonal antibody D3E6, Cell Sig-naling Technology, Inc., Cat #12238), or a commercially available antibody that recognizes a mutant-type carboxyl-terminal sequence (mouse monoclonal antibody CAL2, Dianova GmbH, Cat #DIA-CAL-250). After washing with a TBS-T solution, reaction was performed in a 5% skimmed milk/TBS-T solution containing a peroxidase-labeled anti-rabbit IgG antibody (Santa Cruz Biotechnology, Inc. Cat #sc-2030) or a peroxidase-labeled anti-mouse IgG antibody (Santa Cruz Biotechnology, Inc. Cat #sc-2005) at room temperature for 1 hour. The PVDF membrane was washed with a TBS-T solution and was then reacted with a peroxi-dase luminescence reagent (Thermo Fisher Scientific K.K., Cat #34094). The resulting signals were detected using a FUSION image pickup apparatus (manufactured by Vilber-Lourmat S.A.).

Del 52 type mutant CALR protein having a histidine-tag inserted downstream of the signal sequence at the amino-terminal was expressed in HEK293T cells, and the culture supernatant containing the secreted mutant CALR protein was prepared by centrifugation (15,000 g×10 min, 4° C.). The resulting supernatant was applied to a HisTrap column (GE Healthcare, Cat #17531901), the column was washed with a purification buffer (0.3 M sodium chloride, 25 mM Tris-HCl, pH 7.4) containing 20 mM imidazole, and the mutant CALR protein was purified with a purification buffer containing 50 mM imidazole. The purified protein was reacted with 2-nitro-5-thiocyanobenzoic acid (NTCB) to cyanate the cysteine residue, and then fragmentation was performed under alkaline conditions. The masses of protein fragments were identified using a matrix-assisted laser desorption ionization-time of flight mass spectrometer, and the cleavage site was determined from the peptide sequence information of the Del 52 type mutant CALR protein.

Del 52 type or Ins 5 type mutant CALR protein labeled with a FLAG-tag downstream of the signal sequence at the amino-terminal or labeled with a FLAG-tag at the carboxyl-terminal was expressed in UT-7/TPO cells, and the cells were cultured using an Iscove's Modified Dulbecco's (IMDM) medium containing 10% fetal bovine inactivated serum in 5% $CO_2$ at 37° C. The cells ($1\times10^5$) in the proliferative stage were washed with PBS (phosphate buffer containing 137 mM sodium chloride and 27 mM potassium chloride) and were then reacted with a mouse anti-DYKDDDDK (SEQ ID NO: 35) tag antibody (FUJIFILM Wako Pure Chemical Corporation, Cat #014-22383) or a rat anti-mutant CALR antibody that recognizes the amino-terminal side of the cleavage site in a 2% FBS/PBS solution on ice for 30 minutes. After the reaction, the cells were washed with a 2% FBS/PBS solution and were then reacted with an anti-mouse IgG-Alexa Fluor 647 (Thermo Fisher Scientific K.K., Cat #A21235) and an anti-rat IgG-Alexa Fluor 647 (Thermo Fisher Scientific K.K., Cat #A21247), respectively, as secondary antibodies in a 2% FBS/PBS solution on ice for 30 minutes. After the completion of the reaction, the cells were collected by centrifugation and were reacted with a PBS solution containing 2% paraformaldehyde on ice for 15 minutes. Ultimately, the cells were washed by adding a 2% FBS/PBS solution, then performing centrifugation (400 g×5 min, 4° C.), and discarding the supernatant. Then, 300 ML of a 2% FBS/PBS solution was added to the cells, and signals were quantitatively measured by flow cytometry analysis using FACS Calibur (manufactured by BD biosciences).

Human peripheral blood mononuclear cells were obtained by subjecting peripheral blood collected in a Spitz tube containing an anticoagulant to centrifugation (500 g×10 min, 4° C.), suspending the resulting cell fraction in a PBS solution, then overlaying the suspension on a lymphocyte separation solution Lymphosep (MP biomedicals, Cat #11444815), performing centrifugation (1,500 rpm×30 min, room temperature) to prepare a buffy coat, adding a PBS solution to the resulting buffy coat for resuspension, then performing centrifugation (1,500 rpm×10 min, room temperature), and removing the supernatant. The obtained peripheral blood mononuclear cells were suspended in an RIPA solution (150 mM sodium chloride, 1 mM EDTA, 1% NP-40, 1% sodium deoxycholate, 2 mM sodium orthovanadate (V), 10 mM β-glycerophosphoric acid, 1 μg/mL aprotinin, 2 μg/mL E-64, 1 μg/mL leupeptin, 0.67 μg/mL bestatin, 0.67 μg/mL pepstatin, 43.5 μg/mL PMSF, 20 mM Tris-HCl, pH 7.4) and were then ultrasonicated, followed by centrifugation (15,000 g×15 min, 4° C.). The supernatant was collected as a cell extract. The resulting cell extract was heat-treated in the presence of a reducing agent, then developed on a gel by SDS polyacrylamide electrophoresis, electrically transferred on a polyvinylidene fluoride (PVDF) membrane, and reacted with a TBS-T solution containing 5% skimmed milk at room temperature for 1 hour, followed by reaction with a 5% BSA/TBS-T solution containing a rat anti-mutant CALR antibody that recognizes the amino-terminal side of the cleavage site at 4° C. overnight. After washing with a TBS-T solution, reaction with a 5% skimmed milk/TBS-T solution containing a peroxidase-labeled anti-rat IgG antibody (Santa Cruz Biotechnology, Inc. Cat #sc-2006) was performed at room temperature for 1 hour. The PVDF membrane was washed with a TBS-T solution and was then reacted with a peroxidase luminescence reagent. The resulting signals were detected using a FUSION image pickup apparatus.

Platelets were prepared by subjecting peripheral blood collected in a Spitz tube containing EDTA to centrifugation (500 g×10 min, 4° C.), subjecting the resulting supernatant to centrifugation (2,000 g×15 min, 4° C.), and rinsing the resulting precipitate with 500 μL of a platelet cleaning solution (10 mM sodium citrate, 150 mM sodium chloride, 1 mM EDTA, 1% dextrose, pH 7.4) twice. The obtained platelets were suspended in an RIPA solution and were then ultrasonicated, followed by centrifugation (15,000 g×15 min, 4° C.). The supernatant was collected as a cell extract. The resulting cell extract was heat-treated in the presence of a reducing agent, then developed on a gel by SDS polyacrylamide electrophoresis, electrically transferred on a polyvinylidene fluoride (PVDF) membrane, and reacted with a TBS-T solution containing 5% skimmed milk at room temperature for 1 hour, followed by reaction with a 5% BSA/TBS-T solution containing a rat anti-mutant CALR antibody (B3 antibody) that recognizes the amino-terminal side of the cleavage site at 4° C. overnight. After washing with a TBS-T solution, reaction with a 5% skimmed milk/TBS-T solution containing a peroxidase-labeled anti-rat IgG antibody (Santa Cruz Biotechnology, Inc. Cat #sc-2006) was performed at room temperature for 1 hour. The PVDF membrane was washed with a TBS-T solution and was then reacted with a peroxidase luminescence reagent. The resulting signals were detected using a FUSION image pickup apparatus.

(2) Result

Figure 2:
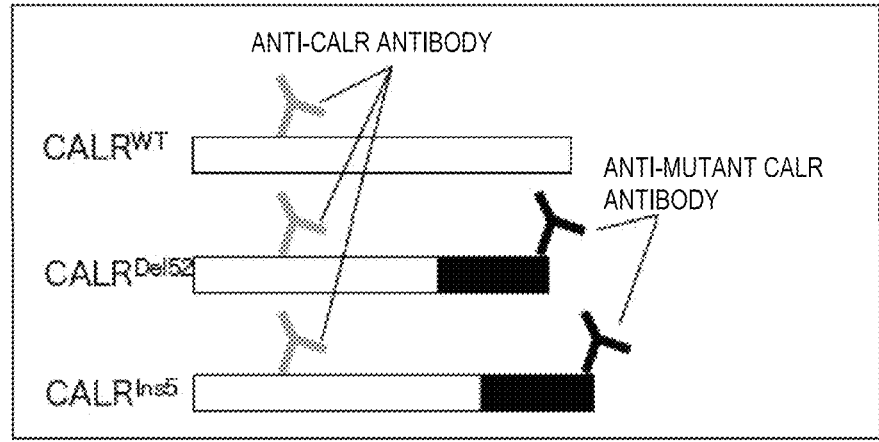
FIG. 2 a diagram showing antibodies that recognize
sequences

CALR proteins contained in the culture supernatants of the UT-7/TPO/CALR Del 52 and UT-7/TPO/CALR Ins 5 cells neoplastically proliferating, the UT-7/TPO/CALR (WT) cells as a control, and the UT-7/TPO/vec cells, which were prepared by transfecting human megakaryoblastic leukemia cell line UT-7/TPO with a vector expressing a Del 52 or Ins 5 type mutant CALR protein, a vector expressing wild-type CALR, and an empty vector, respectively, were evaluated with an antibody that recognizes both the wild-type and the mutant-type (monoclonal antibody D3E6, Cell Signaling Technology, Inc., Cat #12238) and a commercially available antibody that recognizes the mutant-type carboxyl-terminal sequence (monoclonal antibody CAL2, Dianova GmbH, Cat #DIA-CAL-250) (FIG. 2). As a result, the immunoblotting using the antibody (B3 antibody) that recognizes the wild-type and mutant-type CALR proteins detected bands that cannot be recognized by the mutant-type antibody, in addition to the endogenous CALR, in the cells expressing the mutant CALR protein (FIG. 3).

Among peptide fragments obtained by fragmentation using NTCB at the amino-terminal side of the cysteine residue, the peptide fragments found only in the cleavage type of the mutant CALR protein (Del 52 type was used) had molecular weights of 25827.7 and 25418.4. As the cleave sites of the Del 52 type mutant CALR protein, the site between the 380th methionine residue and the 381st arginine residue and the site between the 377th methionine residue and the 378th arginine residue were identified by comparison of the numerical values above and the estimated molecular weights determined from the position of the cleaved cysteine residue.

Del 52 type or Ins 5 type mutant CALR protein labeled with a FLAG tag downstream of the signal sequence at the amino-terminal or labeled with a FLAG tag at the carboxyl-terminal was expressed in UT-7/TPO cells, and the expression of a mutant CALR protein on the cell surfaces were analyzed by flow cytometry using an anti-FLAG antibody. In the cells expressing a mutant CALR protein having the FLAG-tag at the amino-terminal, a stronger signal was observed compared to that in the cells expressing a mutant CALR protein having carboxyl-terminal labeled with the FLAG-tag (FIGS. 4 and 5). Then, flow cytometry analysis of the cell lines used in the analysis shown in FIGS. 4 and 5 was performed using an antibody obtained by immunization with a peptide including a sequence specific to the amino-terminal side of the cleavage site of the mutant CALR protein, resulting in disappearance of the difference in the quantity of detection due to the insertion positions of the FLAG-tag (FIGS. 6 and 7). It has been indicated by this result that setting an antigen-recognition site on the carboxyl-terminal side of the sequence specific to the mutant CALR protein remaining after cleavage is important for creating a more sensitive test reagent or a more powerful therapeutic agent.

Actually, when cell extracts of peripheral blood mononuclear cells and platelets obtained from CALR gene mutation-positive patients were analyzed by immunoblotting using an antibody specific to the amino-terminal side of the cleavage site of a mutant CALR, expression of cleaved mutant CALR protein was observed as in the cell lines (FIG. 8). It has been indicated by these results that the same cleavage actually occurs also in patient's cells and that setting an antigen-recognition site on the carboxyl-terminal side remaining after cleavage is important for creating a more sensitive test reagent or a more powerful therapeutic agent.

Test Example 2

(1) Verification that Three Antibodies Recognize Full-Length and Cleavage Mutant CALR Proteins UT-7/TPO cells expressing a Del 52 type or Ins 5 type mutant CALR protein having a FLAG-tag inserted downstream of the signal sequence at the amino-terminal were cultured, and culture supernatants containing the secreted mutant CALR proteins were prepared by centrifugation (1,600 g×5 min, 4° C.). The resulting culture supernatants were each heat-treated in the presence of SDS and a reducing agent, then developed on a gel by SDS polyacrylamide electrophoresis, electrically transferred on a polyvinylidene fluoride (PVDF) membrane, and reacted with a TBS-T solution containing 5% skimmed milk at room temperature for 1 hour, followed by reaction with a 5% BSA/TBS-T solution containing a rat clone B3, C6, or G1 antibody or a mouse anti-DYKDDDDK (SEQ ID NO: 35) tag antibody (FUJIFILM Wako Pure Chemical Corporation, Cat #014-22383) at 4° C. overnight. After washing with a TBS-T solution, the reaction productions were reacted with a 5% skimmed milk/TBS-T solution containing a peroxidase-labeled goat anti-rat IgG antibody (Jackson Immuno Research Inc., Cat #112-035-003) or a peroxidase-labeled goat anti-mouse IgG antibody (Jackson Immuno Research Inc., Cat #115-035-003) at room temperature for 1 hour. The PVDF membranes were washed with a TBS-T solution and were then reacted with a peroxidase luminescence reagent. The resulting signals were detected using a FUSION image pickup apparatus.

As a result, as shown in FIG. 9, it was verified that all of the clone B3, C6, and G1 antibodies recognize the full-length and cleavage mutant CALR proteins.

(2) Verification that Three Antibodies Recognize Mutant CALR Proteins on Cell Surfaces A Del 52 type or Ins 5 type mutant CALR protein labeled with a FLAG-tag downstream of the signal sequence at the amino-terminal was expressed in UT-7/TPO cells, and the cells were cultured using an IMDM medium containing 10% fetal bovine inactivated serum in 5% $CO_2$ at 37° C. The cells $(1×10^5)$ in the proliferative stage were washed with PBS and were then reacted with a mouse anti-DYKDDDDK (SEQ ID NO: 35) tag antibody (FUJIFILM Wako Pure Chemical Corporation, Cat #014-22383) or a rat clone B3, C6, or G1 antibody in a 2% FBS/PBS solution on ice for 30 minutes. After the reaction, the cells were washed with a 2% FBS/PBS solution and were then reacted with an anti-mouse IgG-Alexa Fluor 647 (Thermo Fisher Scientific K.K., Cat #A21235) and an anti-rat IgG-Alexa Fluor 647 (Thermo Fisher Scientific K.K., Cat #A21247), respectively, as secondary antibodies in a 2% FBS/PBS solution on ice for 30 minutes. After the completion of the reaction, the cells were collected by centrifugation and were reacted with a PBS solution containing 4% paraformaldehyde on ice for 15 minutes. Ultimately, the cells were washed by adding a 2% FBS/PBS solution, then performing centrifugation (400 g×5 min, 4° C.), and discarding the supernatant. Then, 300 ML of a 2% FBS/PBS solution was added to the cells, and signals were quantitatively measured by flow cytometry analysis using FACS Calibur (manufactured by BD biosciences).

As a result, as shown in FIG. 10, it was verified that all of the clone B3, C6, and G1 antibodies recognize the mutant CALR protein on cell surfaces.

Test Example 3

(Evaluation of Avidity of Antibody to Antigen)
(1) Evaluation of Avidity to Antigen by ELISA An ELISA plate (Sumitomo Bakelite Co., Ltd., Cat #MS-8896F) to which 100 ng per well of purified Del 52 type mutant CALR protein or BSA as a control was attached was reacted with PBS containing 5 mg/mL of BSA at room temperature for 1 hour. The wells were washed with PBS and were then reacted with PBS containing 0, 6.25, 12.5, 25, 50, 100, 200, 400, or 800 ng/ml of clone B3, C6, or G1 antibody or rat IgG (Santa Cruz Biotechnology, Inc. Cat #2026) and 5 mg/mL of BSA at room temperature for 1 hour. The wells were washed with PBS and were then reacted with PBS containing 16 ng/ml of peroxidase-labeled goat anti-rat IgG antibody (Jackson Immuno Research Inc., Cat #112-035-003) and 5 mg/mL of BSA at room temperature for 1 hour. After the wells were washed with a TBS-T solution, a TMB solution (Nacalai Tesque, Cat #05298-80) was added to the wells and was allowed to reaction at room temperature for 15 minutes, and 1 M sulfuric acid aqueous solution was then added to the wells. Absorbances at 450 nm and 620 nm were measured, and the difference between the absorbances was determined. The difference in the BSA as a control was subtracted from each difference.

As a result, as shown in FIG. 11, it is demonstrated that the antibodies (B3, C6, and G1) of the present invention all bind to the mutant CALR protein even at low concentrations.

(2) Evaluation of Avidity to Antigen by Surface Plasmon Resonance Analysis

Sensor chips (GE Healthcare, Cat #BR100530) for surface plasmon resonance analysis were loaded on a surface plasmon resonance analyzer Biacore T200 (GE Healthcare) and were equilibrated with an HBS-EP buffer (GE Healthcare, Cat #BR100669). Clone B3 antibody adjusted to a concentration of 10 μg/mL with Acetate 5.5 (GE Healthcare, Cat #BR100352) was immobilized using an Amine coupling kit (GE Healthcare, Cat #BR100050) at an immobilized amount of 200 RU. Subsequently, surface plasmon resonance was measured using a peptide having cysteine at the amino-terminal of the amino acid sequence (RRMMRTKMR) included in SEQ ID NO: 1 adjusted to concentrations of 20, 10, 5, 2.5, and 1.25 nM with an HBS-EP buffer, and the dissociation constant was acquired with Biacore T200 Evaluation Software.

As a result, as shown in FIG. 12, it is demonstrated that the antibody of the present invention strongly binds to the mutant CALR protein.

Test Example 4

(Identification of Antigen-Recognition Site of Antibody)

It was verified that clone B3, C6, and G1 antibodies recognize the amino acid sequence used as an antigen on the mutant CALR protein. The reactivities of the respective antibodies against mutant CALR proteins each having alanine substituted for one amino acid at each position of the amino acids used as the antigen and the amino acids around it were evaluated by immunoblotting (FIG. 13A) and ELISA (FIG. 13B).

(1) Immunoblotting

The Del 52 type mutant CALR proteins each having alanine (A) substituted for one amino acid at each position of the amino acids in the region from the 367th threonine (T) to the 378th arginine (R) or the protein not having substitution were expressed in HEK 293T cells, and culture supernatants containing secreted mutant CALR proteins were prepared by centrifugation (1, 600 g×5 min, 4° C.). The resulting protein solutions were each heat-treated in the presence of SDS and a reducing agent, then developed on a gel by SDS polyacrylamide electrophoresis, electrically transferred on a PVDF membrane, and reacted with a TBS-T solution containing 5% skimmed milk at room temperature for 1 hour, followed by reaction with a 5% BSA/TBS-T solution containing a peroxidase-labeled clone B3, C6, or G1 antibody or a mouse anti-CALR antibody (Abcam plc., Cat #ab22683) at 4° C. overnight. The PVDF membrane reacted with the mouse anti-CALR antibody was washed with a TBS-T solution and was then reacted with a 5% skimmed milk/TBS-T solution containing a peroxidase-labeled anti-mouse IgG antibody (Jackson Immuno Research Inc., Cat #115-035-003) at room temperature for 1 hour. Subsequently, all of the PVDF membranes were washed with a TBS-T solution and were then reacted with a peroxidase luminescence reagent (Thermo Fisher Scientific K.K., Cat #34094). The resulting signals were detected using a FUSION image pickup apparatus (manufactured by Vilber-Lourmat S.A.).

As a result, as shown in FIG. 13A, it was demonstrated that the antibodies of the present invention recognize the site between the 1st arginine and the 9th arginine of SEQ ID NO: 1.

(2) ELISA

An ELISA plate to which the mutant CALR proteins prepared by the above-described method were attached was reacted with PBS containing 5 mg/mL of BSA at room temperature for 1 hour. The wells were washed with PBS and were then reacted with PBS containing 200 ng/ml of clone B3, C6, or G1 antibody or a mouse anti-CALR antibody (Santa Cruz Biotechnology, Inc., Cat #sc-373863) and 5 mg/mL of BSA at room temperature for 1 hour. The wells were washed with PBS and were then reacted with PBS containing 16 ng/ml of peroxidase-labeled goat anti-rat IgG antibody (Jackson Immuno Research Inc., Cat #112-035-003) or goat anti-mouse IgG antibody (Santa Cruz Biotechnology, Inc., Cat #sc-2005) and 5 mg/mL of BSA at room temperature for 1 hour. After washing the wells with a TBS-T solution, a TMB solution was added to the wells and was allowed to reaction at room temperature for 15 minutes, and 1 M sulfuric acid aqueous solution was then added to the wells. Absorbances at 450 nm and 620 nm were measured, and the difference between the absorbances was determined.

As a result, as shown in FIG. 13B, it was demonstrated that the antibodies of the present invention recognize the site between the 1st arginine and the 9th arginine of SEQ ID NO: 1.

Test Example 5

(Determination of Sequence Information of Antibody of the Present Invention)

As the sequence information of the heavy-chain and light-chain of the antibodies (B3, C6, and G1) of the present invention, the full-length sequences of cDNAs of the heavy-chain and the light-chain were determined by preparing mRNAs from cells producing the antibodies using a PureLinc RNA Mini kit (Thermo Fisher Scientific K.K., Cat #12183025), synthesizing cDNAs using the resulting mRNAs as templates and reverse transcription primers specific to the heavy-chain and the light-chain by a rapid amplification of cDNA ends method, then cloning the cDNAs in plasmids, and analyzing the plasmids by sanger sequencing.

The results are shown in FIGS. 14 to 17 and SEQ ID NOs: 5 to 34.

FIG. 14 shows the amino acid sequences of the heavy-chain variable regions of the antibodies (B3, C6, and G1) of the present invention. FIG. 15 shows the amino acid sequences of the light-chain variable regions of the antibodies (B3, C6, and G1) of the present invention. FIG. 16 shows the nucleotide sequences of the heavy-chain variable regions of the antibodies (B3, C6, and G1) of the present invention. FIG. 17 shows the nucleotide sequences of the light-chain variable regions of the antibodies (B3, C6, and G1) of the present invention.

SEQ ID NO: 5 shows the amino acid sequence of the heavy-chain variable region of B3 antibody. SEQ ID NO: 6 shows the amino acid sequence of the heavy-chain variable region of C6 antibody. SEQ ID NO: 7 shows the amino acid sequence of the heavy-chain variable region of G1 antibody. SEQ ID NO: 8 shows the amino acid sequence of the light-chain variable region of B3 antibody. SEQ ID NO: 9 shows the amino acid sequence of the light-chain variable region of C6 antibody. SEQ ID NO: 10 shows the amino acid sequence of the light-chain variable region of G1 antibody.

SEQ ID NO: 11 shows the nucleotide sequence of the heavy-chain variable region of B3 antibody. SEQ ID NO: 12 shows the nucleotide sequence of the heavy-chain variable region of C6 antibody. SEQ ID NO: 13 shows the nucleotide sequence of the heavy-chain variable region of G1 antibody. SEQ ID NO: 14 shows the nucleotide sequence of the light-chain variable region of B3 antibody. SEQ ID NO: 15 shows the nucleotide sequence of the light-chain variable region of C6 antibody. SEQ ID NO: 16 shows the nucleotide sequence of the light-chain variable region of G1 antibody.

SEQ ID NO: 17 shows the amino acid sequence of CDR1 of VH of B3 antibody. SEQ ID NO: 18 shows the amino acid sequence of CDR2 of VH of B3 antibody. SEQ ID NO: 19 shows the amino acid sequence of CDR3 of VH of B3 antibody. SEQ ID NO: 20 shows the amino acid sequence of CDR1 of VH of C6 antibody. SEQ ID NO: 21 shows the amino acid sequence of CDR2 of VH of C6 antibody. SEQ ID NO: 22 shows the amino acid sequence of CDR3 of VH of C6 antibody. SEQ ID NO: 23 shows the amino acid sequence of CDR1 of VH of G1 antibody. SEQ ID NO: 24 shows the amino acid sequence of CDR2 of VH of G1 antibody. SEQ ID NO: 25 shows the amino acid sequence of CDR3 of VH of G1 antibody. SEQ ID NO: 26 shows the amino acid sequence of CDR1 of VL of B3 antibody. SEQ ID NO: 27 shows the amino acid sequence of CDR2 of VL of B3 antibody. SEQ ID NO: 28 shows the amino acid sequence of CDR3 of VL of B3 antibody. SEQ ID NO: 29 shows the amino acid sequence of CDR1 of VL of C6 antibody. SEQ ID NO: 30 shows the amino acid sequence of CDR2 of VL of C6 antibody. SEQ ID NO: 31 shows the amino acid sequence of CDR3 of VL of C6 antibody. SEQ ID NO: 32 shows the amino acid sequence of CDR1 of VL of G1 antibody. SEQ ID NO: 33 shows the amino acid sequence of CDR2 of VL of G1 antibody. SEQ ID NO: 34 shows the amino acid sequence of CDR3 of VL of G1 antibody.

Test Example 6

(Evaluation of Therapeutic Effect)

A chimeric B3 antibody was produced by fusing the variable regions of the heavy-chain and light-chain of clone B3 antibody and the constant regions of the heavy-chain and light-chain of corresponding mouse IgG2a and was administered to myeloproliferative neoplasm model mice produced by grafting hematopoietic stem cells expressing Del 52 type CALR mutant gene, and the therapeutic effect of the chimeric antibody was evaluated.

An expression vector containing a B3 mouse chimeric heavy-chain and light-chain gene ligated with a gene sequence encoding the heavy-chain variable region of clone B3 antibody and the constant region of mouse IgG2a or a gene sequence encoding the light-chain variable region of clone B3 antibody and the constant region of mouse immu-noglobulin κ was transfected into ExpiCHO-S cells (Thermo Fisher Scientific K.K., Cat #A29127), and the cells were cultured using an ExpiCHO Expression medium (Thermo Fisher Scientific K.K., Cat #A2910001) in 5% $CO_2$ at 37° C. for 10 days. The culture supernatants were collected by centrifugation (4,000 g×30 min, 4° C.) and were each applied to a HiTrap Protein G HP column (GE Healthcare, Cat #29048581) for attaching the chimeric antibody to the column, followed by elution using 0.1 M Glycine-HCl (pH 2.7). The elution fractions neutralized with 1 M Tris-HCl (pH 9.0) were dialyzed to PBS to prepare B3 mouse chimeric antibodies.

In evaluation of the therapeutic effect of the B3 mouse chimeric antibody, bone marrow transplanted model mice were used. Bone marrow cells were purified from thigh-bones of 8- to 10-week old B6.CD45.1 congenic mice (Sankyo Labo Service Corporation, Inc.), and c-kit positive cells labeled with an APC-labeled anti-c-kit antibody were isolated, and further LSK cells being Ter119, CD4, CD8, Gr-1, CD45R, CD3e, and CD11b negative and CD117 and Sca1 positive were isolated. The cells were infected with a retrovirus containing a pMSCV-IRES-GFP vector express-ing the Del 52 type mutant CALR gene or a control vector. Seventy-two hours after the infection, 4,000 LSK cells per mouse were transplanted to 8- to 10-week old C57BL/6J mice (Oriental Yeast Co., Ltd.) irradiated with a radiation at 6 Gray twice. The number of platelets in peripheral blood was counted over time with an automated multi-channel blood cell counter (Sysmex Corporation, Cat #pocH-100iV Diff). In the two months after the transplantation, after verification of thrombocytosis, which is the phenotype of a myeloproliferative neoplasm that is caused by expression of the mutant CALR gene, the B3 mouse chimeric antibody or a solvent (PBS) was administered at 250 μg per mouse every week from 9 weeks after the transplantation, and the throm-bocytosis-suppressing effect specific to the B3 mouse chi-meric antibody was evaluated.

As a result, as shown in FIG. 18, the antibody of the present invention showed excellent therapeutic effect on an MPN.

The invention claimed is:

1. An antibody or a functional fragment thereof that binds to a cleaved mutant CALR polypeptide, said antibody or functional fragment thereof selected from the group consisting of (c), (d), and (e):

(c) an antibody in which CDR1, CDR2, and CDR3 of the immunoglobulin VH chain are polypeptides consisting of the amino acid sequences set forth in SEQ ID NOs: 17, 18, and 19, respectively, and CDR1, CDR2, and CDR3 of the immunoglobulin VL chain are polypeptides consisting of the amino acid sequences set forth in SEQ ID NOs: 26, 27, and 28, respectively;

(d) an antibody in which CDR1, CDR2, and CDR3 of the immunoglobulin VH chain are polypeptides consisting of the amino acid sequences set forth in SEQ ID NOs: 20, 21, and 22, respectively; and CDR1, CDR2, and CDR3 of the immunoglobulin VL chain are polypeptides consisting of the amino acid sequences set forth in SEQ ID NOs: 29, 30, and 31, respectively; and (e) an antibody in which CDR1, CDR2, and CDR3 of the immunoglobulin VH chain are polypeptides consisting of the amino acid sequences set forth in SEQ ID NOs: 23, 24, and 25, respectively; and CDR1, CDR2, and CDR3 of the immunoglobulin VL chain are polypeptides consisting of the amino acid sequences set forth in SEQ ID NOs: 32, 33, and 34, respectively.

2. The antibody or functional fragment thereof of claim 1, selected from the group consisting of (C), (D), and (E):

(C) an antibody comprising an immunoglobulin VH chain consisting of an amino acid sequence set forth in SEQ ID NO: 5 or an amino acid sequence having a deletion, substitution, or addition of up to one amino acid in the amino acid sequence set forth in SEQ ID NO: 5; and an immunoglobulin VL chain consisting of an amino acid sequence set forth in SEQ ID NO: 8 or an amino acid sequence having a deletion, substitution, or addition of up to one amino acid in the amino acid sequence set forth in SEQ ID NO: 8;

(D) an antibody comprising an immunoglobulin VH chain consisting of an amino acid sequence set forth in SEQ ID NO: 6 or an amino acid sequence having a deletion, substitution, or addition of up to one amino acid in the amino acid sequence set forth in SEQ ID NO: 6; and an immunoglobulin VL chain consisting of an amino acid sequence set forth in SEQ ID NO: 9 or an amino acid sequence having a deletion, substitution, or addition of up to one amino acid in the amino acid sequence set forth in SEQ ID NO: 9; and (E) an antibody comprising an immunoglobulin VH chain consisting of an amino acid sequence set forth in SEQ ID NO: 7 or an amino acid sequence having a deletion, substitution, or addition of up to one amino acid in the amino acid sequence set forth in SEQ ID NO: 7; and an immunoglobulin VL chain consisting of an amino acid sequence set forth in SEQ ID NO: 10 or an amino acid sequence having a deletion, substitution, or addition of up to one amino acid in the amino acid sequence set forth in SEQ ID NO: 10.

3. A composition, comprising:

the antibody or functional antibody fragment of claim 1, formulated for therapy of a myeloproliferative neoplasm (MPN) or formulated for use in a method of diagnosing myeloproliferative neoplasm.

4. A method for detecting a mutant CALR polypeptide comprising, contacting the antibody or functional antibody fragment of claim 1 with a sample comprising:

a polypeptide consisting of an amino acid sequence set forth in SEQ ID NO: 1 and detecting complex formation, thereby detecting said polypeptide.

5. A method for detecting a mutant CALR polypeptide, comprising:

contacting the antibody or functional antibody fragment of claim 1 with a polypeptide consisting of an amino acid sequence set forth in SEQ ID NO: 1;

and detecting complex formation between the antibody or functional fragment and said polypeptide;

wherein complex formation is indicative of presence of the mutant CALR polypeptide.

6. The method of detecting of claim 4, further comprising identifying a therapeutic agent for MPN comprising contacting the therapeutic agent with a polypeptide consisting of an amino acid sequence set forth in SEQ ID NO: 1;

and measuring complex formation, wherein complex formation is indicative of a therapeutic effect on MPN.

7. A therapeutic method for a myeloproliferative neoplasm (MPN), the method comprising:

administering the antibody or functional antibody fragment of claim 1 to a subject in need thereof.

8. The antibody or fragment of claim 1, comprising the antigen-recognition site in the polypeptide chain consisting of the amino acid sequence set forth in SEQ ID NO: 1.

9. The antibody or functional fragment of claim 1, comprising (c) an antibody in which CDR1, CDR2, and CDR3 of the immunoglobulin VH chain are polypeptides consisting of the amino acid sequences set forth in SEQ ID NOs: 17, 18, and 19, respectively; and CDR1, CDR2, and CDR3 of the immunoglobulin VL chain are polypeptides consisting of the amino acid sequences set forth in SEQ ID NOs: 26, 27, and 28, respectively.

10. The antibody or functional fragment of claim 1, comprising (d) an antibody in which CDR1, CDR2, and CDR3 of the immunoglobulin VH chain are polypeptides consisting of the amino acid sequences set forth in SEQ ID NOs: 20, 21, and 22, respectively; and CDR1, CDR2, and CDR3 of the immunoglobulin VL chain are polypeptides consisting of the amino acid sequences set forth in SEQ ID NOs: 29, 30, and 31, respectively.

11. The antibody or functional fragment of claim 1, comprising (e) an antibody in which CDR1, CDR2, and CDR3 of the immunoglobulin VH chain are polypeptides consisting of the amino acid sequences set forth in SEQ ID NOs: 23, 24, and 25, respectively; and CDR1, CDR2, and CDR3 of the immunoglobulin VL chain are polypeptides consisting of the amino acid sequences set forth in SEQ ID NOs: 32, 33, and 34, respectively.

12. The method of claim 4 comprising (i) detecting said polypeptide in a biological sample containing a drug.

* * * * *

SEQUENCE LISTING

```
<160> NUMBER OF SEQ ID NOS: 35

<210> SEQ ID NO 1
<211> LENGTH: 13
<212> TYPE: PRT
<213> ORGANISM: Homo sapiens

<400> SEQUENCE: 1

Arg Arg Met Met Arg Thr Lys Met Arg Met Arg Arg Met
1               5                   10

<210> SEQ ID NO 2
<211> LENGTH: 417
<212> TYPE: PRT
<213> ORGANISM: Homo sapiens

<400> SEQUENCE: 2

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
```

-continued

```
            35                    40                    45
Phe Val Leu Ser Ser Gly Lys Phe Tyr Gly Asp Glu Glu Lys Asp Lys
    50                    55                    60

Gly Leu Gln Thr Ser Gln Asp Ala Arg Phe Tyr Ala Leu Ser Ala Ser
65                    70                    75                    80

Phe Glu Pro Phe Ser Asn Lys Gly Gln Thr Leu Val Val Gln Phe Thr
                    85                    90                    95

Val Lys His Glu Gln Asn Ile Asp Cys Gly Gly Gly Tyr Val Lys Leu
                100                   105                   110

Phe Pro Asn Ser Leu Asp Gln Thr Asp Met His Gly Asp Ser Glu Tyr
                115                   120                   125

Asn Ile Met Phe Gly Pro Asp Ile Cys Gly Pro Gly Thr Lys Lys Val
    130                   135                   140

His Val Ile Phe Asn Tyr Lys Gly Lys Asn Val Leu Ile Asn Lys Asp
145                   150                   155                   160

Ile Arg Cys Lys Asp Asp Glu Phe Thr His Leu Tyr Thr Leu Ile Val
                165                   170                   175

Arg Pro Asp Asn Thr Tyr Glu Val Lys Ile Asp Asn Ser Gln Val Glu
                180                   185                   190

Ser Gly Ser Leu Glu Asp Asp Trp Asp Phe Leu Pro Pro Lys Lys Ile
                195                   200                   205

Lys Asp Pro Asp Ala Ser Lys Pro Glu Asp Trp Asp Glu Arg Ala Lys
    210                   215                   220

Ile Asp Asp Pro Thr Asp Ser Lys Pro Glu Asp Trp Asp Lys Pro Glu
225                   230                   235                   240

His Ile Pro Asp Pro Asp Ala Lys Lys Pro Glu Asp Trp Asp Glu Glu
                245                   250                   255

Met Asp Gly Glu Trp Glu Pro Pro Val Ile Gln Asn Pro Glu Tyr Lys
                260                   265                   270

Gly Glu Trp Lys Pro Arg Gln Ile Asp Asn Pro Asp Tyr Lys Gly Thr
                275                   280                   285

Trp Ile His Pro Glu Ile Asp Asn Pro Glu Tyr Ser Pro Asp Pro Ser
    290                   295                   300

Ile Tyr Ala Tyr Asp Asn Phe Gly Val Leu Gly Leu Asp Leu Trp Gln
305                   310                   315                   320

Val Lys Ser Gly Thr Ile Phe Asp Asn Phe Leu Ile Thr Asn Asp Glu
                325                   330                   335

Ala Tyr Ala Glu Glu Phe Gly Asn Glu Thr Trp Gly Val Thr Lys Ala
                340                   345                   350

Ala Glu Lys Gln Met Lys Asp Lys Gln Asp Glu Glu Gln Arg Leu Lys
                355                   360                   365

Glu Glu Glu Glu Asp Lys Lys Arg Lys Glu Glu Glu Glu Ala Glu Asp
                370                   375                   380

Lys Glu Asp Asp Glu Asp Lys Asp Glu Asp Glu Glu Asp Glu Glu Asp
385                   390                   395                   400

Lys Glu Glu Asp Glu Glu Glu Asp Val Pro Gly Gln Ala Lys Asp Glu
                405                   410                   415

Leu
```

<210> SEQ ID NO 3
<211> LENGTH: 411
<212> TYPE: PRT
<213> ORGANISM: Homo sapiens -continued

```
<400> SEQUENCE: 3

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
                20                  25                  30

Trp Thr Ser Arg Trp Ile Glu Ser Lys His Lys Ser Asp Phe Gly Lys
            35                  40                  45

Phe Val Leu Ser Ser Gly Lys Phe Tyr Gly Asp Glu Glu Lys Asp Lys
        50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
        130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
            195                 200                 205

Lys Asp Pro Asp Ala Ser Lys Pro Glu Asp Trp Asp Glu Arg Ala Lys
        210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
            245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Pro Ser
        290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Thr Arg
            355                 360                 365

Arg Met Met Arg Thr Lys Met Arg Met Arg Met Arg Arg Thr Arg
        370                 375                 380

Arg Lys Met Arg Arg Lys Met Ser Pro Ala Arg Pro Arg Thr Ser Cys
385                 390                 395                 400

Arg Glu Ala Cys Leu Gln Gly Trp Thr Glu Ala
            405                 410
```

```
<210> SEQ ID NO 4
<211> LENGTH: 430
<212> TYPE: PRT
<213> ORGANISM: Homo sapiens

<400> SEQUENCE: 4

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
        130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
            195                 200                 205

Lys Asp Pro Asp Ala Ser Lys Pro Glu Asp Trp Asp Glu Arg Ala Lys
        210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Pro Ser
        290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
            355                 360                 365

Glu Glu Glu Glu Asp Lys Lys Arg Lys Glu Glu Glu Glu Ala Glu Asp
```

```
            370             375             380

Asn Cys Arg Arg Met Met Arg Thr Lys Met Arg Met Arg Arg Met Arg
385                 390                 395                 400

Arg Thr Arg Arg Lys Met Arg Arg Lys Met Ser Pro Ala Arg Pro Arg
                405                 410                 415

Thr Ser Cys Arg Glu Ala Cys Leu Gln Gly Trp Thr Glu Ala
                420                 425                 430

<210> SEQ ID NO 5
<211> LENGTH: 119
<212> TYPE: PRT
<213> ORGANISM: Rattus norvegicus

<400> SEQUENCE: 5

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Arg Asn
                20                  25                  30

Phe Ile His Trp Ile Lys Gln Gln Pro Gly Asn Gly Leu Glu Trp Ile
            35                  40                  45

Gly Trp Ile Phe Pro Gly Asp Gly Asp Thr Glu Tyr Asn Gln Lys Phe
        50                  55                  60

Asn Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asn Tyr Asn Tyr Glu Tyr Phe Asp Tyr Trp Gly Gln Gly
            100                 105                 110

Val Met Val Thr Val Ser Ser
        115

<210> SEQ ID NO 6
<211> LENGTH: 121
<212> TYPE: PRT
<213> ORGANISM: Rattus norvegicus

<400> SEQUENCE: 6

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Tyr
                20                  25                  30

Phe Val His Trp Ile Lys Gln Gln Pro Gly Asp Gly Leu Glu Trp Ile
            35                  40                  45

Gly Trp Ile Tyr Pro Gly Asp Gly Asp Thr Glu Tyr Asn His Lys Phe
        50                  55                  60

Asn Gly Lys Ser Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asn Tyr Tyr Asp Gly Arg Glu Val Met Asp Ala Trp Gly
            100                 105                 110

Gln Gly Ala Ser Val Thr Val Ser Ser
        115                 120

<210> SEQ ID NO 7
<211> LENGTH: 121
<212> TYPE: PRT
```

<213> ORGANISM: Rattus norvegicus

<400> SEQUENCE: 7

```
Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Tyr
            20                  25                  30

Phe Val His Trp Ile Lys Gln Gln Pro Gly Asp Gly Leu Glu Trp Ile
        35                  40                  45

Gly Trp Ile Tyr Pro Gly Asp Gly Asp Thr Glu Tyr Asn Gln Lys Phe
    50                  55                  60

Asn Gly Lys Ala Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asn Tyr Tyr Asp Gly Arg Glu Val Met Asp Ala Trp Gly
            100                 105                 110

Gln Gly Ala Ser Val Thr Val Ser Ser
        115                 120
```

<210> SEQ ID NO 8
<211> LENGTH: 107
<212> TYPE: PRT
<213> ORGANISM: Rattus norvegicus

<400> SEQUENCE: 8

```
Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Asp Ile Tyr Ser Tyr
            20                  25                  30

Leu Ala Trp Tyr Gln Gln Lys Pro Gly Lys Ser Pro Gln Leu Leu Ile
        35                  40                  45

Phe Ala Ala Asn Arg Leu Gln Asp Gly Val Pro Ser Arg Phe Ser Gly
    50                  55                  60

Ser Gly Ser Gly Thr Gln Phe Ser Leu Lys Ile Ser Gly Met Gln Pro
65                  70                  75                  80

Glu Asp Glu Gly Asp Tyr Phe Cys Leu Gln Gly Ser Lys Phe Pro Tyr
                85                  90                  95

Thr Phe Gly Pro Gly Thr Lys Leu Glu Leu Asn
            100                 105
```

<210> SEQ ID NO 9
<211> LENGTH: 112
<212> TYPE: PRT
<213> ORGANISM: Rattus norvegicus

<400> SEQUENCE: 9

```
Asp Val Val Leu Thr Gln Thr Pro Pro Thr Leu Ser Ala Thr Ile Gly
1               5                   10                  15

Gln Ser Val Ser Ile Ser Cys Arg Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Gln Leu Leu Ile Tyr Ser Val Ser Asn Leu Glu Ser Gly Val Pro
    50                  55                  60

Asn Arg Phe Ser Gly Ser Gly Ser Glu Thr Asp Phe Thr Leu Lys Ile
65                  70                  75                  80
```

Ser Gly Met Glu Ala Glu Asp Leu Gly Val Tyr Tyr Cys Met Gln Ala
                85                  90                  95

Thr His Gly Pro Tyr Thr Phe Gly Ala Gly Thr Lys Leu Glu Leu Lys
            100                 105                 110

<210> SEQ ID NO 10
<211> LENGTH: 112
<212> TYPE: PRT
<213> ORGANISM: Rattus norvegicus

<400> SEQUENCE: 10

Asp Val Val Leu Thr Gln Thr Pro Pro Thr Leu Ser Ala Thr Ile Gly
1               5                   10                  15

Gln Ser Val Ser Ile Ser Cys Arg Ser Ser Gln Ser Leu Leu Asp Ser
            20                  25                  30

Asp Gly Glu Thr Tyr Leu Asn Trp Leu Leu Gln Arg Pro Gly Gln Cys
        35                  40                  45

Pro Gln Leu Leu Ile Tyr Ser Val Ser Asn Leu Glu Ser Gly Val Pro
    50                  55                  60

Asn Arg Phe Ser Gly Ser Gly Ser Glu Thr Asp Phe Thr Leu Lys Ile
65                  70                  75                  80

Ser Gly Val Glu Ala Glu Asp Leu Gly Val Tyr Tyr Cys Met Gln Gly
                85                  90                  95

Thr His Gly Pro Tyr Thr Phe Gly Ala Gly Thr Lys Leu Glu Leu Lys
            100                 105                 110

<210> SEQ ID NO 11
<211> LENGTH: 357
<212> TYPE: DNA
<213> ORGANISM: Rattus norvegicus

<400> SEQUENCE: 11
caggtacagc tgcagcaatc tgggggctgaa ctggtgaagc ctgggtcctc agtgaaaatt      60
tcctgcaagg cttctggcta caccttcacc cgtaacttta tacactggat aaaacagcag     120
cctggaaatg gccttgagtg gattgggtgg attttttcctg agatggtga tacagagtac     180 aatcaaaagt tcaatgggaa ggcaacactc actgcagaca aatcgtccag cacagcctat     240
atgcagctca gcagcctgac atctgaggac tctgcagtct atttctgtgc aagaggaaat     300
tacaactacg agtactttga ttactggggc caaggagtca tggtcacagt ctcctca       357

<210> SEQ ID NO 12
<211> LENGTH: 363
<212> TYPE: DNA
<213> ORGANISM: Rattus norvegicus

<400> SEQUENCE: 12
caggtacagc tgcagcaatc tgggggctgaa ctggtgaagc ctgggtcctc agtgaaaatt      60
tcctgcaagg cttctggcta caccttcacc agttactttg tgcactggat aaaacagcag     120
cctggagatg gccttgagtg gattgggtgg atttatcctg agatggtga tacagagtac     180 aatcacaagt tcaatgggaa gtcaacactc actgcagaca gatcctccag tacagcctat     240
atgcagctca gcagcctgac atctgaggac tctgcagtct atttctgtgc aagagggaat     300
tactatgatg gtcgggaagt tatggatgcc tggggtcaag gagcttcagt cactgtctcc     360
tca                                                                    363

-continued

```
<210> SEQ ID NO 13
<211> LENGTH: 363
<212> TYPE: DNA
<213> ORGANISM: Rattus norvegicus

<400> SEQUENCE: 13
caggtacagc tgcagcaatc tgggggctgaa ctggtgaagc ctgggtcctc agtgaaaatt      60
tcctgcaagg cttctggcta caccttcacc agttactttg tgcactggat aaaacagcag     120
cctggagatg gccttgagtg gattgggtgg atttatcctg agatggtga tacagagtac      180 aatcaaaagt tcaatgggaa ggcaacactc actgcagaca atcctccag tacagcctat       240 atgcagctca gcagcctgac atctgaggac tctgcagtct atttctgtgc aagagggaat      300
tactatgatg gtcgggaagt tatggatgcc tgggggtcaag gagcttcagt cactgtctcc     360
tca                                                                    363

<210> SEQ ID NO 14
<211> LENGTH: 321
<212> TYPE: DNA
<213> ORGANISM: Rattus norvegicus

<400> SEQUENCE: 14
gacatccaga tgacacagtc tccggcttcc ctgtctgcat ctctgggaga aactgtctcc      60
atcgagtgtc tagcaagtga ggacatttac agttatttag catggtatca acagaagcca     120
gggaaatctc ctcagctcct gatctttgct gcaaataggt tgcaagatgg ggtcccatca      180
cggttcagtg gcagtggatc tggcacacag ttttctctca agatcagcgg catgcaacct      240
gaagatgaag gggattattt ctgtctacag ggttccaagt ttccgtacac ctttggacct     300
gggaccaagc tggaactgaa c                                                321

<210> SEQ ID NO 15
<211> LENGTH: 336
<212> TYPE: DNA
<213> ORGANISM: Rattus norvegicus

<400> SEQUENCE: 15
gatgttgtgc tgacccagac tccacccact ttatcggcta ccattggaca atcggtctcc      60
atctcttgca ggtcaagtca gagtctctta gatagtgatg agaaaccta tttaaattgg      120 ttgctacaga ggccaggcca atctccacag cttctaattt attcggtctc caacctggaa      180
tctggggtcc ccaacaggtt cagtggcagt gggtcagaaa cagatttcac actcaaaatc      240
agtggaatgg aggctgaaga tttgggagtt tactactgca tgcaagctac ccatggtccg      300
tacacgtttg gagctgggac caagctggaa ctgaaa                                336

<210> SEQ ID NO 16
<211> LENGTH: 336
<212> TYPE: DNA
<213> ORGANISM: Rattus norvegicus

<400> SEQUENCE: 16
gatgttgtgc tgacccagac tccacccact ttatcggcta ccattggaca atcggtctcc      60
atctcttgca ggtcaagtca gagtctctta gatagtgatg agaaaccta tttaaattgg      120 ttgctacaga ggccaggcca atgtccacag cttctaattt attcggtatc caacctggaa      180
tctggggtcc ccaacaggtt cagtggcagt gggtcagaaa cagatttcac actcaaaatc      240
agtggagtgg aggctgaaga tttgggagtt tactactgca tgcaaggtac ccatggtccg      300
```

```
tacacgtttg gagctgggac caagctggaa ctgaaa                                    336
```

```
<210> SEQ ID NO 17
<211> LENGTH: 10
<212> TYPE: PRT
<213> ORGANISM: Rattus norvegicus

<400> SEQUENCE: 17

Gly Tyr Thr Phe Thr Arg Asn Phe Ile His
1               5                   10

<210> SEQ ID NO 18
<211> LENGTH: 17
<212> TYPE: PRT
<213> ORGANISM: Rattus norvegicus

<400> SEQUENCE: 18

Trp Ile Phe Pro Gly Asp Gly Asp Thr Glu Tyr Asn Gln Lys Phe Asn
1               5                   10                  15

Gly

<210> SEQ ID NO 19
<211> LENGTH: 10
<212> TYPE: PRT
<213> ORGANISM: Rattus norvegicus

<400> SEQUENCE: 19

Gly Asn Tyr Asn Tyr Glu Tyr Phe Asp Tyr
1               5                   10

<210> SEQ ID NO 20
<211> LENGTH: 10
<212> TYPE: PRT
<213> ORGANISM: Rattus norvegicus

<400> SEQUENCE: 20

Gly Tyr Thr Phe Thr Ser Tyr Phe Val His
1               5                   10

<210> SEQ ID NO 21
<211> LENGTH: 17
<212> TYPE: PRT
<213> ORGANISM: Rattus norvegicus

<400> SEQUENCE: 21

Trp Ile Tyr Pro Gly Asp Gly Asp Thr Glu Tyr Asn His Lys Phe Asn
1               5                   10                  15

Gly

<210> SEQ ID NO 22
<211> LENGTH: 12
<212> TYPE: PRT
<213> ORGANISM: Rattus norvegicus

<400> SEQUENCE: 22

Gly Asn Tyr Tyr Asp Gly Arg Glu Val Met Asp Ala
1               5                   10

<210> SEQ ID NO 23
<211> LENGTH: 10
<212> TYPE: PRT
<213> ORGANISM: Rattus norvegicus

<400> SEQUENCE: 23
```

-continued

```
Gly Tyr Thr Phe Thr Ser Tyr Phe Val His
1               5                   10

<210> SEQ ID NO 24
<211> LENGTH: 17
<212> TYPE: PRT
<213> ORGANISM: Rattus norvegicus

<400> SEQUENCE: 24

Trp Ile Tyr Pro Gly Asp Gly Asp Thr Glu Tyr Asn Gln Lys Phe Asn
1               5                   10                  15

Gly

<210> SEQ ID NO 25
<211> LENGTH: 12
<212> TYPE: PRT
<213> ORGANISM: Rattus norvegicus

<400> SEQUENCE: 25

Gly Asn Tyr Tyr Asp Gly Arg Glu Val Met Asp Ala
1               5                   10

<210> SEQ ID NO 26
<211> LENGTH: 11
<212> TYPE: PRT
<213> ORGANISM: Rattus norvegicus

<400> SEQUENCE: 26

Leu Ala Ser Glu Asp Ile Tyr Ser Tyr Leu Ala
1               5                   10

<210> SEQ ID NO 27
<211> LENGTH: 7
<212> TYPE: PRT
<213> ORGANISM: Rattus norvegicus

<400> SEQUENCE: 27

Ala Ala Asn Arg Leu Gln Asp
1               5

<210> SEQ ID NO 28
<211> LENGTH: 9
<212> TYPE: PRT
<213> ORGANISM: Rattus norvegicus

<400> SEQUENCE: 28

Leu Gln Gly Ser Lys Phe Pro Tyr Thr
1               5

<210> SEQ ID NO 29
<211> LENGTH: 16
<212> TYPE: PRT
<213> ORGANISM: Rattus norvegicus

<400> SEQUENCE: 29

Arg Ser Ser Gln Ser Leu Leu Asp Ser Asp Gly Glu Thr Tyr Leu Asn
1               5                   10                  15

<210> SEQ ID NO 30
<211> LENGTH: 7
<212> TYPE: PRT
<213> ORGANISM: Rattus norvegicus

<400> SEQUENCE: 30
```

-continued

```
Ser Val Ser Asn Leu Glu Ser
1               5

<210> SEQ ID NO 31
<211> LENGTH: 9
<212> TYPE: PRT
<213> ORGANISM: Rattus norvegicus

<400> SEQUENCE: 31

Met Gln Ala Thr His Gly Pro Tyr Thr
1               5

<210> SEQ ID NO 32
<211> LENGTH: 16
<212> TYPE: PRT
<213> ORGANISM: Rattus norvegicus

<400> SEQUENCE: 32

Arg Ser Ser Gln Ser Leu Leu Asp Ser Asp Gly Glu Thr Tyr Leu Asn
1               5                   10                  15

<210> SEQ ID NO 33
<211> LENGTH: 7
<212> TYPE: PRT
<213> ORGANISM: Rattus norvegicus

<400> SEQUENCE: 33

Ser Val Ser Asn Leu Glu Ser
1               5

<210> SEQ ID NO 34
<211> LENGTH: 9
<212> TYPE: PRT
<213> ORGANISM: Rattus norvegicus

<400> SEQUENCE: 34

Met Gln Gly Thr His Gly Pro Tyr Thr
1               5

<210> SEQ ID NO 35
<211> LENGTH: 8
<212> TYPE: PRT
<213> ORGANISM: Artificial
<220> FEATURE:
<223> OTHER INFORMATION: Synthetic peptide

<400> SEQUENCE: 35

Asp Tyr Lys Asp Asp Asp Asp Lys
1               5
```